(12) United States Patent
Inaoka et al.

(10) Patent No.: US 11,752,227 B2
(45) Date of Patent: Sep. 12, 2023

(54) ULTRAVIOLET IRRADIATION UNIT AND ULTRAVIOLET STERTILIZATION DEVICE

(71) Applicant: Enplas Corporation, Saitama (JP)

(72) Inventors: Natsuki Inaoka, Kawaguchi (JP); Hayate Kawano, Kawaguchi (JP); Tetsuya Tokiwa, Kawaguchi (JP)

(73) Assignee: Enplas Corporation (JP), Saitama (JP)

( * ) Notice: Subject to any disclaimer, the term of this patent is extended or adjusted under 35 U.S.C. 154(b) by 0 days.

(21) Appl. No.: 17/302,100

(22) Filed: Apr. 23, 2021

(65) Prior Publication Data

US 2021/0236673 A1   Aug. 5, 2021

Related U.S. Application Data

(63) Continuation of application No. PCT/JP2019/042048, filed on Oct. 25, 2019.

(30) Foreign Application Priority Data

Nov. 2, 2018 (JP) ................................ 2018-207395
Mar. 28, 2019 (JP) ................................ 2019-063231
Jul. 23, 2019 (JP) ................................ 2019-135582

(51) Int. Cl.
*A61L 2/10* (2006.01)
*A61L 9/20* (2006.01)
*C02F 1/32* (2023.01)

(52) U.S. Cl.
CPC .................... *A61L 2/10* (2013.01); *A61L 9/20* (2013.01); *C02F 1/325* (2013.01); *A61L 2202/11* (2013.01); *C02F 2201/3228* (2013.01)

(58) Field of Classification Search
None
See application file for complete search history.

(56) References Cited

U.S. PATENT DOCUMENTS

2019/0241445 A1* 8/2019 Watanabe ................ A61L 2/10
2019/0247559 A1   8/2019 Mochizuki

FOREIGN PATENT DOCUMENTS

| CN | 208135922 U | 11/2018 |
|---|---|---|
| CN | 109415228 A | 3/2019 |
| CN | 109890432 A | 6/2019 |
| EP | 3533480 A1 | 9/2019 |
| JP | 2016-531746 A | 10/2016 |
| JP | 2017-225925 A | 12/2017 |
| JP | 2018-34020 A | 3/2018 |
| JP | 2018-64771 A | 4/2018 |
| JP | 2018-68442 A | 5/2018 |
| JP | 2018-118201 A | 8/2018 |
| JP | 2019-98055 A | 6/2019 |

(Continued)

OTHER PUBLICATIONS

International Search Report and Written Opinion for PCT/JP2019/042048, dated Dec. 10, 2019, 10 pages.

*Primary Examiner* — Andrew Smyth
(74) *Attorney, Agent, or Firm* — Lee & Hayes, P.C.

(57) ABSTRACT

An ultraviolet irradiation unit of the present invention includes a casing, a light source emitting ultraviolet rays arranged in the casing, an ultraviolet transmitting body arranged between an ultraviolet emission opening of the casing and the light source. The casing has an outer diameter dimension that enables the casing to fit within a bore of a joint connected to a flow channel pipe.

3 Claims, 32 Drawing Sheets

(56) References Cited

FOREIGN PATENT DOCUMENTS

| | | | |
|---|---|---|---|
| KR | 20190020659 A | 3/2019 | |
| TW | 201827345 A | 8/2018 | |
| WO | 2015031739 A1 | 3/2015 | |
| WO | WO-2017052067 A1 * | 3/2017 | ............ A61L 2/10 |
| WO | 2017221733 A1 | 12/2017 | |
| WO | WO-2017221733 A1 * | 12/2017 | ............ B01J 47/04 |
| WO | 2018074359 A1 | 4/2018 | |
| WO | WO-2018074359 A1 * | 4/2018 | ............ A61L 2/10 |
| WO | 2018079406 A1 | 5/2018 | |

\* cited by examiner

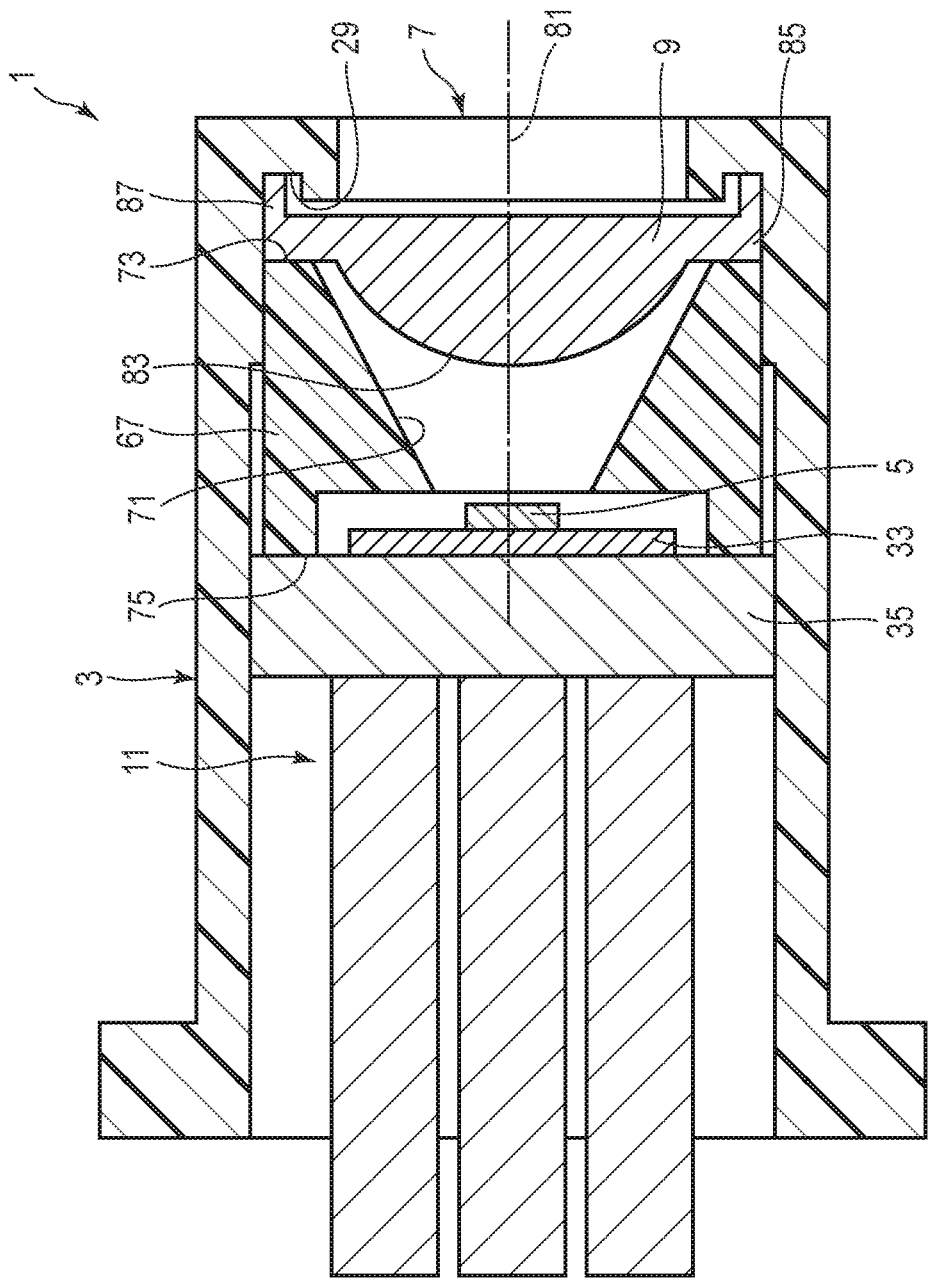
F I G. 5

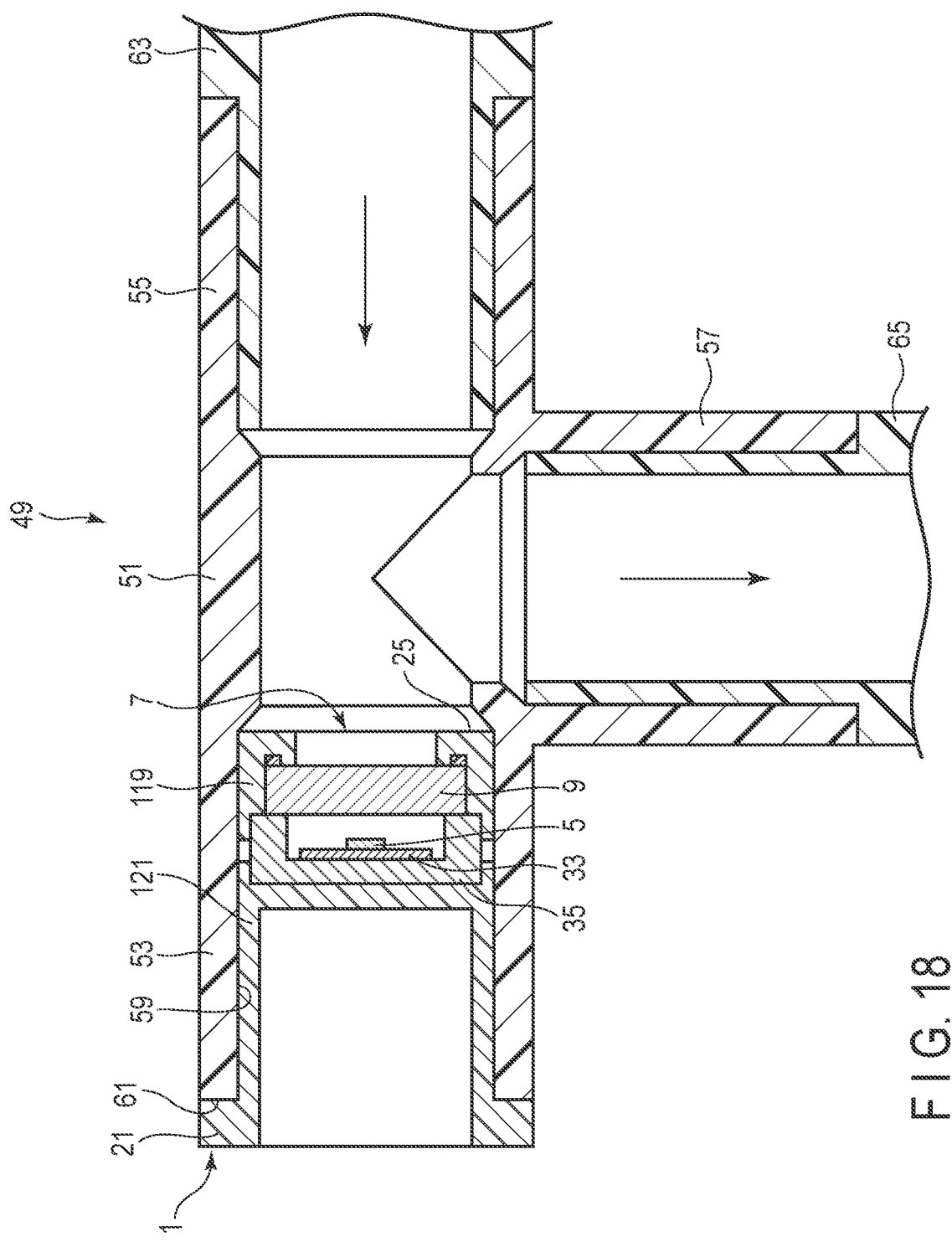
F I G. 18

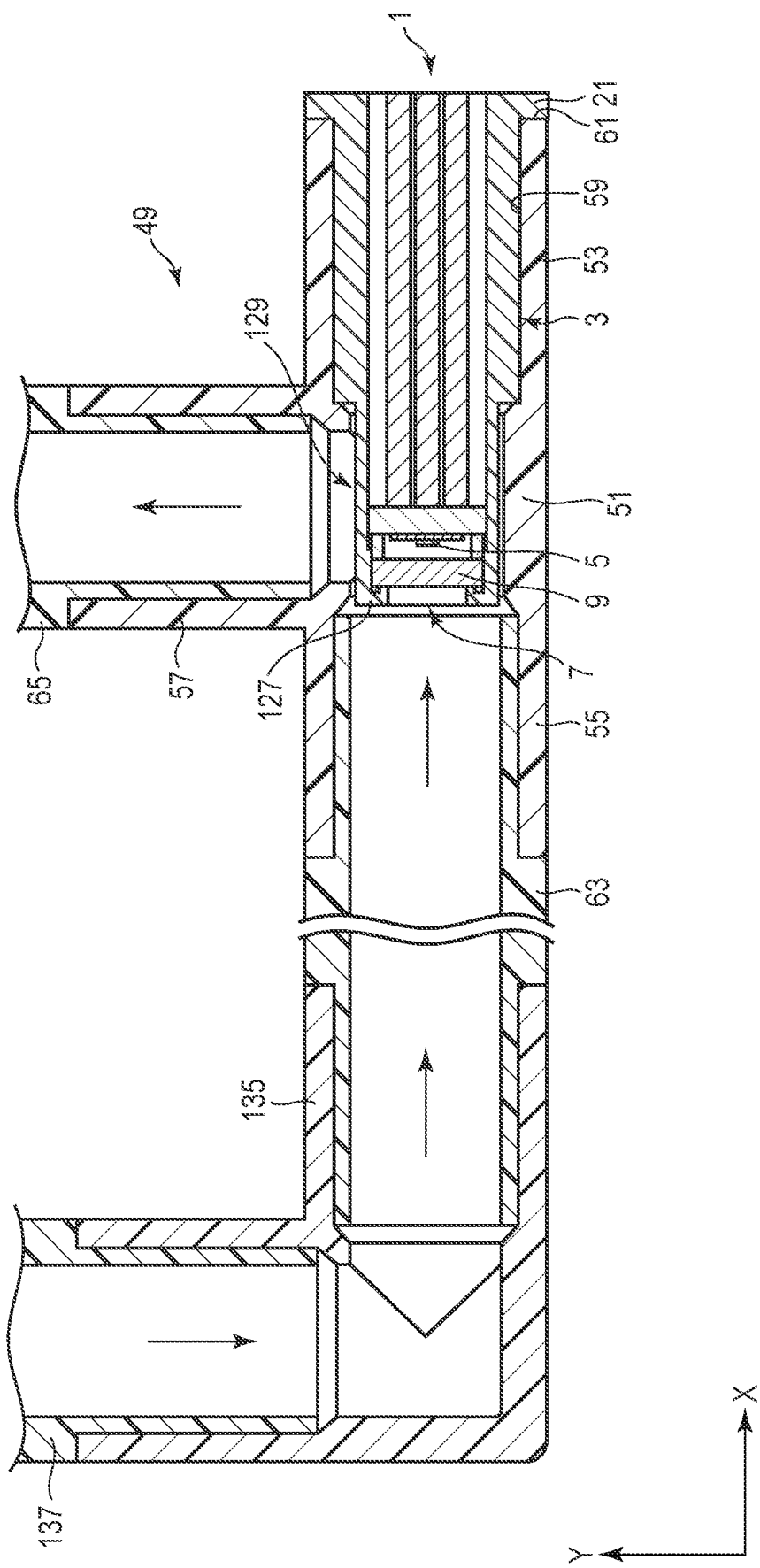
F I G. 24

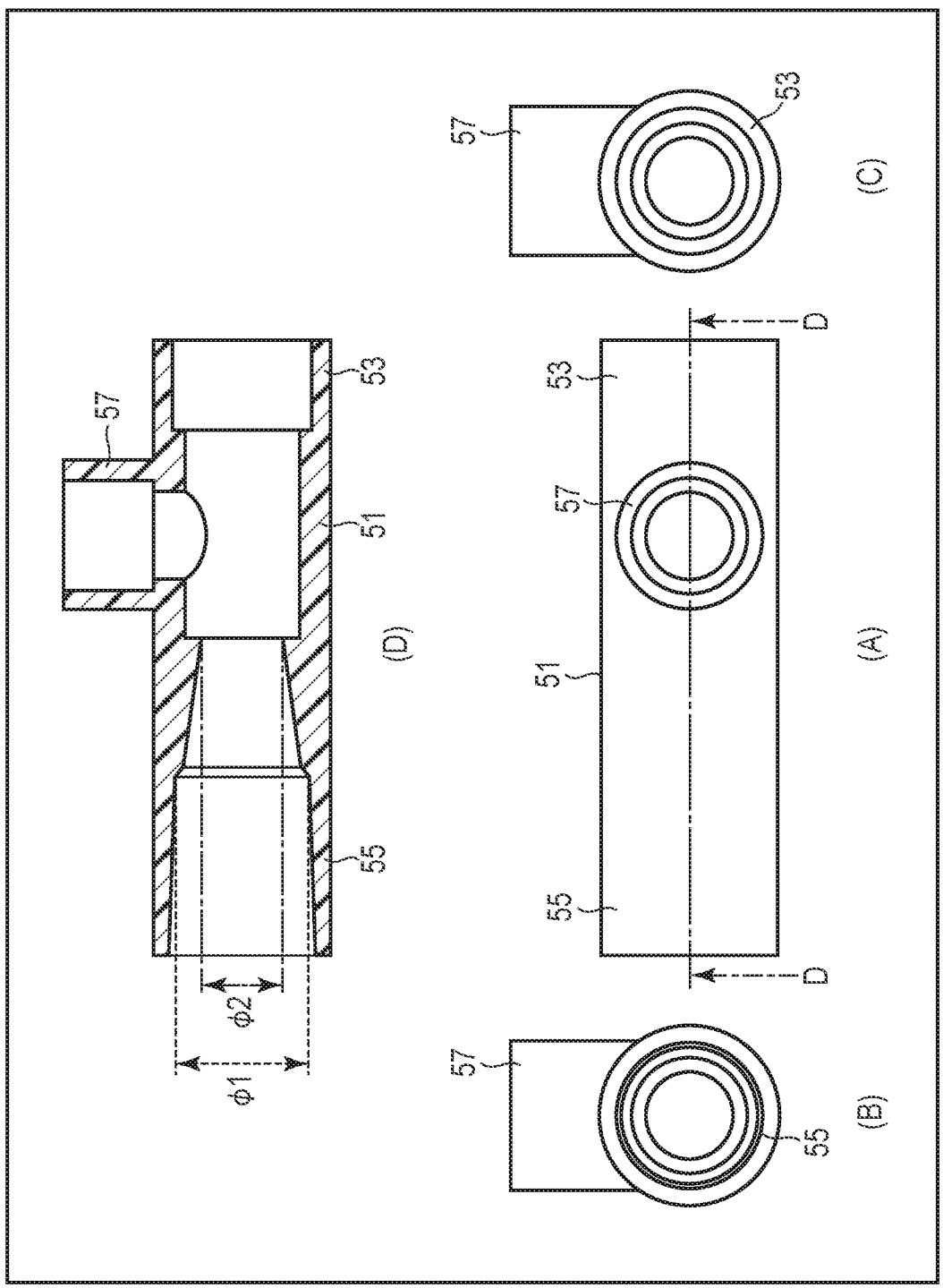
F I G. 26

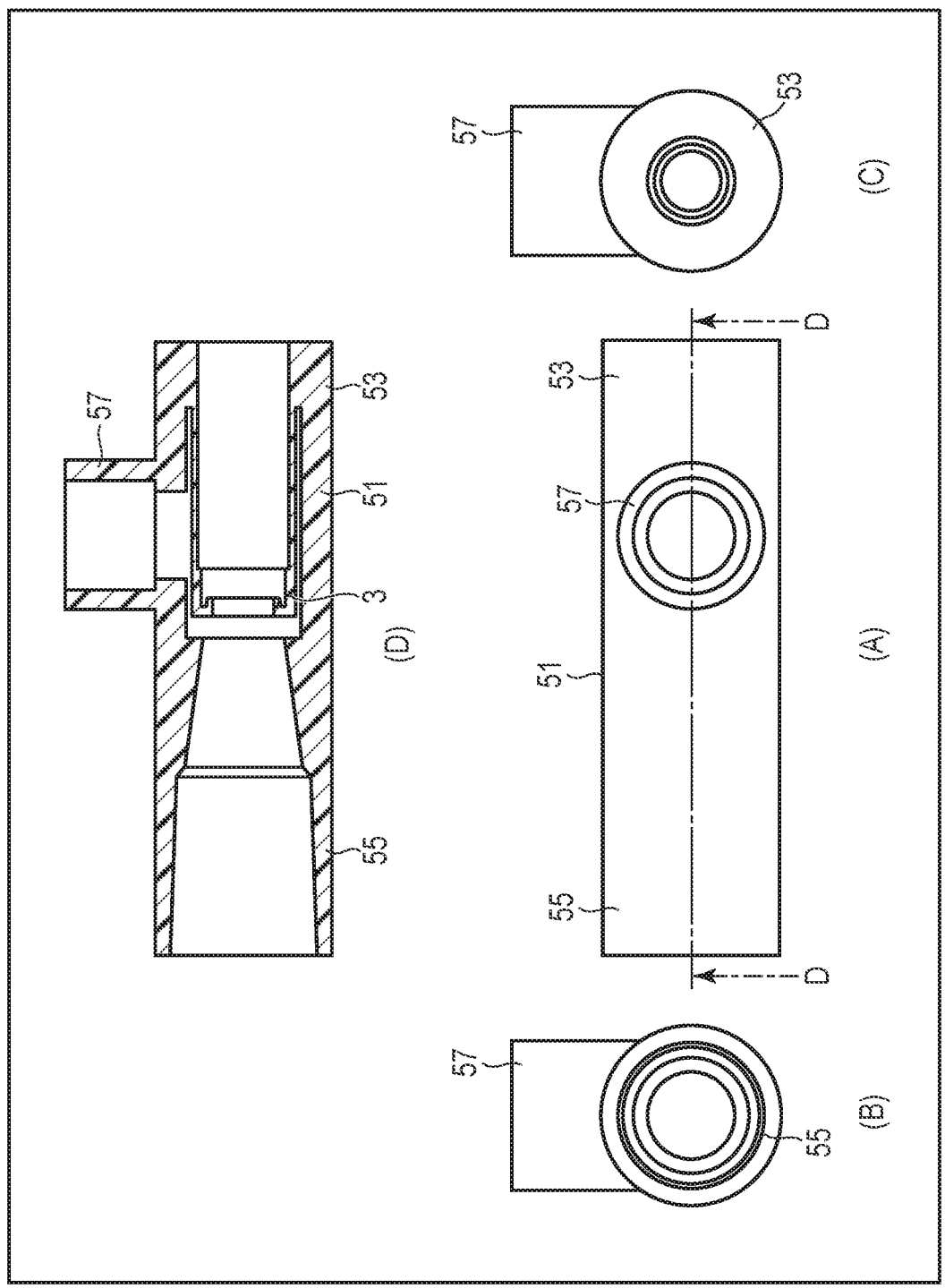
F I G. 31

ULTRAVIOLET IRRADIATION UNIT AND ULTRAVIOLET STERILIZATION DEVICE

CROSS-REFERENCE TO RELATED APPLICATIONS

This application is a Continuation Application of PCT Application No. PCT/JP2019/042048, filed Oct. 25, 2019 and based upon and claiming the benefit of priority from prior Japanese Patent Applications No. 2018-207395, filed Nov. 2, 2018; No. 2019-063231, filed Mar. 28, 2019; and No. 2019-135582, filed Jul. 23, 2019, the entire contents of all of which are incorporated herein by reference.

BACKGROUND OF THE INVENTION

1. Field of the Invention

The present invention relates generally to an ultraviolet irradiation unit and an ultraviolet sterilization device.

2. Description of the Related Art

It is widely known that ultraviolet rays are used to sterilize a fluid in a flow channel pipe. For example, JP 2016-531746 A discloses an ultraviolet sterilizer that uniformly disperses ultraviolet rays to sterilize the fluid in the flow channel tube.

BRIEF SUMMARY OF THE INVENTION

However, when sterilizing the fluid flowing through the existing flow path pipe, it is difficult to connect a conventional ultraviolet sterilization device to the existing flow channel pipe, and separate connection facilities are required.

The present invention described herein aim to provide an ultraviolet irradiation unit and an ultraviolet sterilization device that can easily be connected to an existing flow channel pipe.

To solve the problem, the ultraviolet irradiation unit of the present invention includes a casing, a light source emitting ultraviolet rays arranged in the casing, an ultraviolet transmitting body arranged between an ultraviolet emission opening of the casing and the light source. The casing has an outer diameter dimension that enables the casing to fit within a bore of a joint connected to a flow channel pipe.

In addition, to solve the above problem, in the ultraviolet sterilization device of the present invention, the ultraviolet irradiation unit is fitted in one mouth portion of a joint including three or more mouth portions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a cross-sectional view showing an ultraviolet irradiation unit of Embodiment 3.

FIG. 18 is a cross-sectional view showing an ultraviolet sterilization device comprising an ultraviolet irradiation unit of Embodiment 8.

FIG. 24 is cross-sectional view showing an ultraviolet sterilization device according to Embodiment 12.

FIG. 26 is a diagram showing a joint of an ultraviolet irradiation device of Embodiment 13, where part (A) is a plan view, part (B) is a left side view, part (C) is a right side view, and part (D) is a cross-sectional view taken along line D-D shown in part (A).

FIG. 31 is a diagram showing a joint of an ultraviolet irradiation device of Modified Example 3, where part (A) is a plan view, part (B) is a left side view, part (C) is a right side view, and part (D) is a cross-sectional view taken along line D-D shown in part (A).

DETAILED DESCRIPTION OF THE INVENTION

Embodiments of the present invention will be described hereinafter with reference to the accompanying drawings.

Embodiment 1

Figure 1:
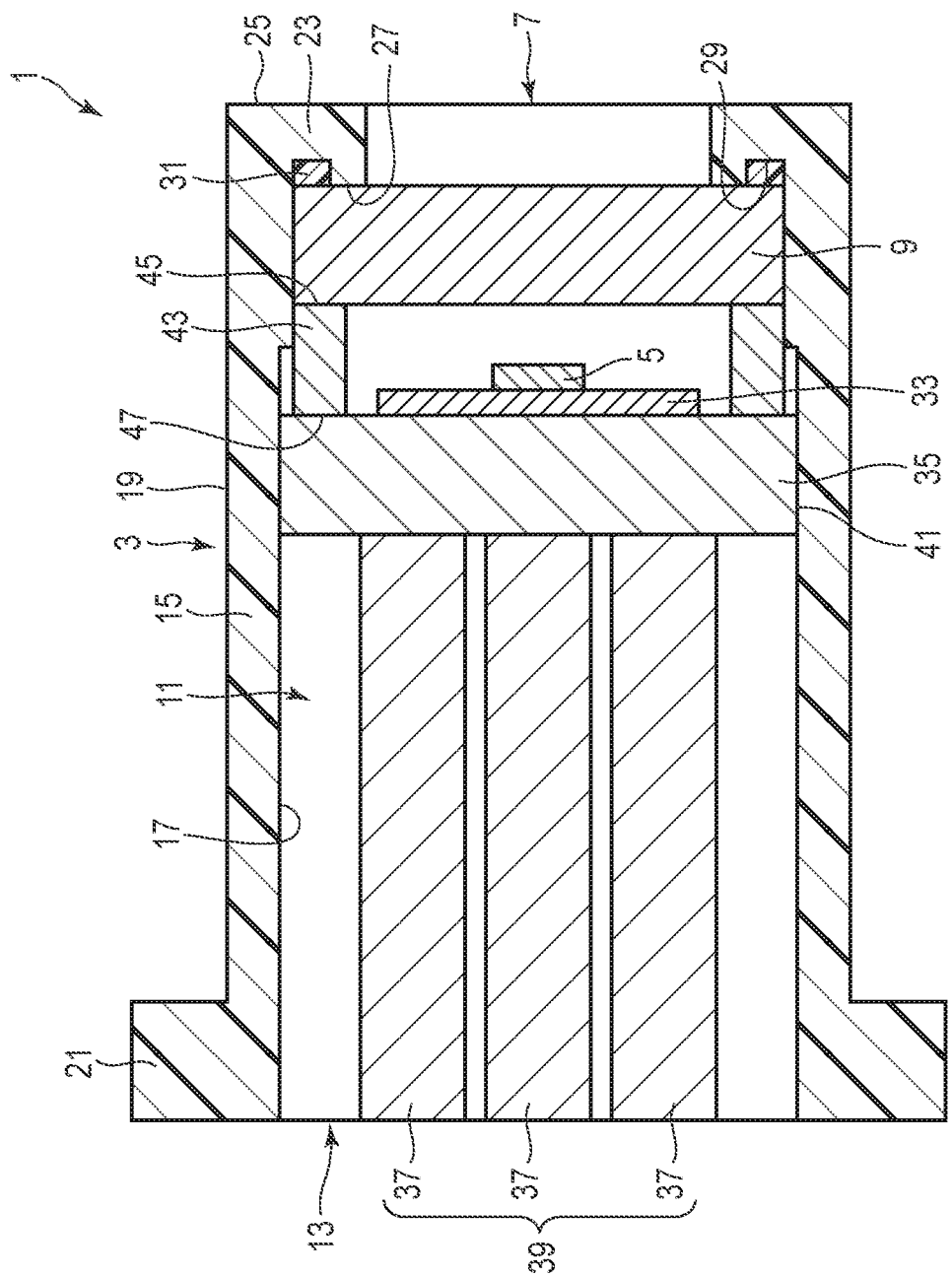
FIG. 1 is a cross-sectional view showing an ultraviolet irradiation unit of Embodiment 1 of the present invention.
Figure 2:
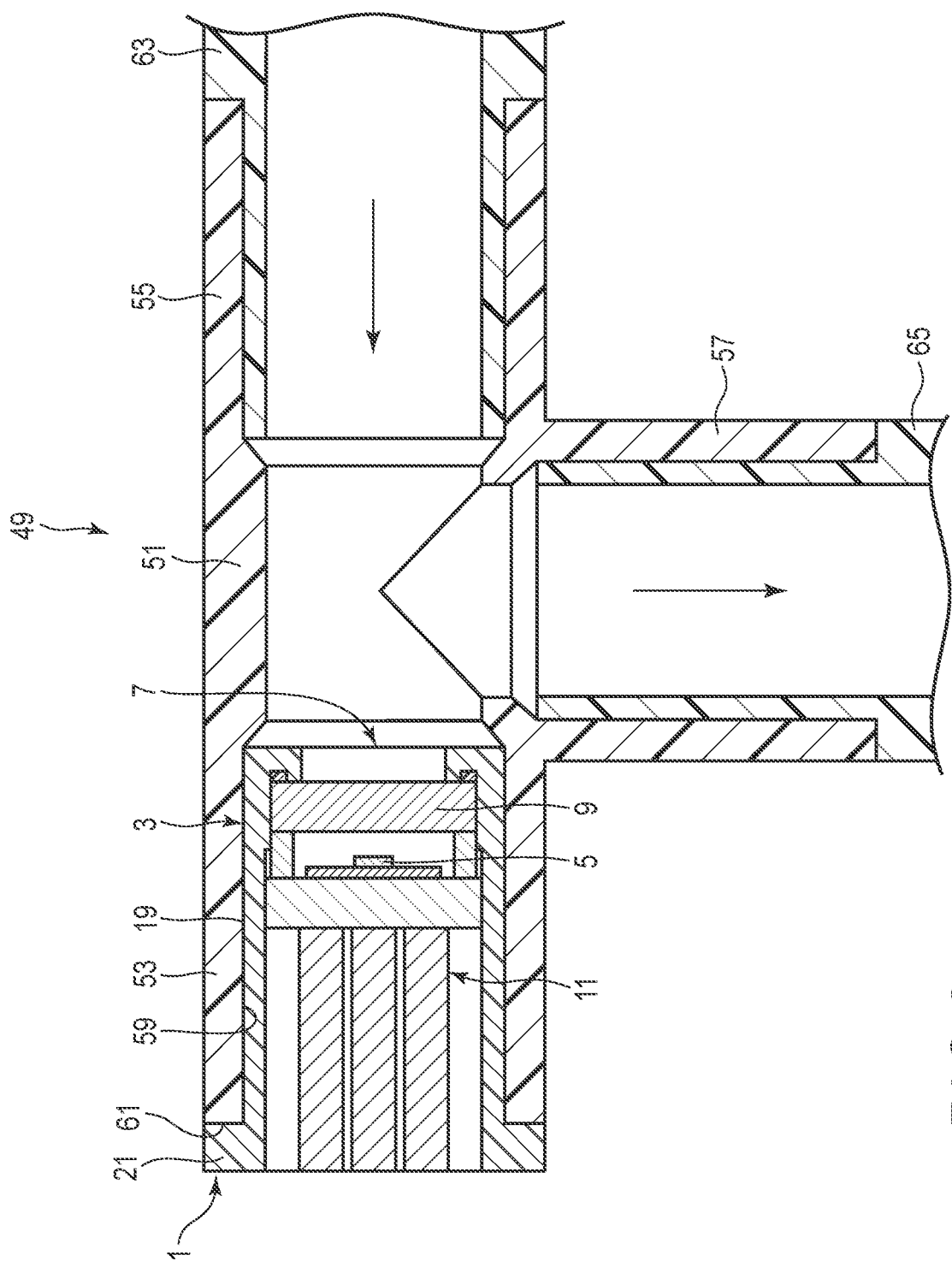
FIG. 2 is a cross-sectional view showing an ultraviolet sterilization device of the embodiment.

As shown in FIG. 1 and FIG. 2, an ultraviolet irradiation unit 1 includes a substantially cylindrical casing 3, a light source 5 disposed in the casing 3, an ultraviolet transmitting body 9 disposed between an ultraviolet emission opening 7 of the casing 3 and the light source 5.

The casing 3 has an outer diameter dimension that enables the casing to fit within a bore of a joint connected to a flow channel pipe, and includes a substantially cylindrical casing body 15 comprising an ultraviolet emission opening 7 and a module insertion opening 13 through which an ultraviolet irradiation module 11 comprising the light source 5 is inserted.

The casing 3 is formed of, for example, a resin material such as vinyl chloride, polypropylene (PP), crosslinked polyethylene, or polyphenylene sulfide (PPS), a resin material containing a material having a high thermal conductivity such as carbon black, or a metal material such as stainless steel, bronze, which is an alloy of copper and tin, brass, which is an alloy of copper and zinc, or aluminum. The casing 3 is desirably formed of the same material as a joint 51 to be described later.

The module insertion opening 13 is opened to be large as compared with the ultraviolet emission opening 7. The module insertion opening 13 has, for example, a circular shape with a diameter of 21 mm. The ultraviolet emission opening 7 has, for example, a circular shape with a diameter of 14 mm.

The casing body 15 has an outer diameter dimension that enables the casing body to fit within a bore of an opening of the joint 51 to be described later. The outer diameter of the casing body 15 is an outer diameter that meets the standard of the joint to be connected, and is set to be, for example, an outer diameter that enables the casing body to be connected to the JIS K6743 TS cheese joint nominal diameter 20, in this embodiment. An inner wall 17 of the casing body 15 is provided with a thread groove (not shown) in which the ultraviolet irradiation module 11 is screwed. An outer wall 19 of the casing body 15 is provided with a thread groove (not shown) that screws in an inner wall 59 of a first mouth portion 53 of the joint 51 to be described later.

In addition, the casing body 15 includes a flange portion 21 at an end part on the module insertion opening 13 side and an extending portion 23 at an end part on the ultraviolet emission opening 7 side.

The flange portion 21 is provided to extend from the end part of the casing body 15 on the module insertion opening 13 side toward the outer peripheral side. The flange portion 21 abuts on an opening side end portion 61 of the first mouth portion 53 of the joint 51 to be described later, and prevents the ultraviolet irradiation unit 1 from entirely entering the first mouth portion 53 of the joint 51.

The extension portion 23 is provided to extend from the end part of the casing body 15 on the side of the ultraviolet emission opening 7 toward the inner peripheral side so as to narrow the diameter of the ultraviolet emission opening 7, and then extend toward the inside of the hollow of the casing body 15. The extending portion 23 includes a fluid contact portion 25, an ultraviolet transmitting body abutting portion 27, and a packing insertion groove 29 formed between the ultraviolet transmitting body abutting portion 27 and the inner wall 17 of the casing body 15. The ultraviolet transmitting body abutting portion 27 abuts on the ultraviolet transmitting body 9 together with packing 31 arranged in the packing insertion groove 29.

The packing 31 is an O-ring and is formed of, for example, nitrile rubber, fluororubber, ethylene propylene rubber, silicone rubber, or acrylic rubber.

The ultraviolet irradiation module 11 includes a light source 5, a substrate 33 arranged on the surface of the light source 5 on the module insertion opening 13 side, a base 35 arranged on the surface of the substrate 33 on the module insertion opening 13 side, and a heat radiating body 39 comprising a plurality of heat radiating plates 37 arranged at intervals on the surface of the base 35 on the module insertion opening 13 side and spaced apart at intervals.

The light source 5 emits ultraviolet rays. The center wavelength or peak wavelength of the ultraviolet rays emitted from the light source 5 is, for example, 200 nm or more and 350 nm or less. The center wavelength or peak wavelength of the ultraviolet rays emitted from the light source 5 is desirably 260 nm or more and 290 nm or less from the viewpoint of high sterilization efficiency. The type of the light source 5 is not particularly limited as long as it can emit ultraviolet rays. The type of the light source 5 is, for example, a light emitting diode (LED), a mercury lamp, a metal halide lamp, a xenon lamp, or a laser diode (LD).

The base 35 has a circular plate shape, and a side wall 41 is provided with a screw groove (not shown) that is screwed with the inner wall 17 of the casing 3. The base 35 is formed of, for example, a resin material containing carbon black or a material having a high thermal conductivity such as aluminum (Al).

Each of the heat radiating plates 37 radiates the heat generated from the light source 5 to the outside. Each of the heat radiating plates 37 is formed of, for example, a material having a high thermal conductivity such as aluminum, iron, or copper. Each of the heat radiating plates 37 can improve the heat radiating performance by increasing the surface area like a sword and a bellows. In addition, by using a resin material containing carbon black or a material having a high thermal conductivity such as aluminum (Al) for the casing 3, continuous heat transfer between the fluid and the casing 3 and the heat radiating plates 37 can be promoted and the heat radiating performance can be further improved.

The ultraviolet light transmitting body 9 enables the ultraviolet light emitted from the light source 5 to be transmitted into the joint 51. The ultraviolet transmitting body 9 abuts on the ultraviolet transmissive body abutting portion 27 and the packing 31 of the casing 3 and is fitted into the casing body 15. The ultraviolet transmitting body 9 is formed of, for example, a material having a high ultraviolet transmissivity, such as quartz ($SiO_2$), sapphire ($Al_2O_3$), an amorphous fluorine resin, or a silicone resin. The ultraviolet transmitting body is, for example, a plate-shaped body or a condenser lens containing one or more materials selected from the above-mentioned materials.

A spacer 43 is provided between the light source 5 and the ultraviolet transmitting body 9. One end 45 of the spacer 43 is in contact with the vicinity of the outer periphery of the surface of the ultraviolet transmitting body 9 on the module insertion opening 13 side and is fixed such that the ultraviolet transmitting body 9 is not displaced. In addition, the other end 47 of the spacer 43 is in contact with the vicinity of the outer periphery of the surface of the base 35 of the ultraviolet irradiation module 11 on the side of the ultraviolet emission opening 7, and the light source 5 thereby comes into contact with the ultraviolet transmitting body 9 and positions the ultraviolet transmitting body 9 to prevent the body from being damaged.

The above-described ultraviolet irradiation module 11 can be attached to the casing 3 by inserting the light source 5 from the module insertion opening 13 toward the hollow of the casing body 15, screwing the inner wall 17 of the casing 3 and the side wall 41 of the base 35 of the ultraviolet irradiation module 11, and making the vicinity of the outer periphery of the base 35 abut on the other end 47 of the spacer 43. For this reason, the ultraviolet irradiation module 11 is detachably provided in the casing 3.

As shown in FIG. 2, in an ultraviolet sterilization device 49, the ultraviolet irradiation unit 1 is fitted in the first mouth portion 53 which is one mouth portion of the joint 51 including three mouth portions.

The joint 51 is, for example, a commercially available joint, and is formed of a resin material such as vinyl chloride, polypropylene, crosslinked polyethylene, or a metal material such as stainless steel, bronze, or brass. The joint 51 is desirably formed of the same material as the casing 3. The joint 51 is, for example, a joint having three or more mouth portions, such as a joint having three mouth portions in a T-shape, a Y-shape or the like and a joint having four mouth portions in a cross shape.

The joint 51 is a T-shaped joint, and has a first mouth portion 53 opening to one end side in the longitudinal direction, a second mouth portion 55 opening to the other end side in the longitudinal direction, and a third mouth portion 57 branching vertically from the vicinity of the center in the longitudinal direction and opening. In other words, the joint 51 having three mouth portions includes a first mouth portion 53 and a second mouth portion 55 that are arranged to face each other, a pipe that connects the first mouth portion 53 and the second mouth portion 55, and a third mouth portion 57 having an opening in the pipe.

A screw groove (not shown) provided on the inner wall 59 of the first mouth portion 53 and a screw groove provided on the outer wall 19 of the casing body 15 of the ultraviolet irradiation unit 1 are screwed into the first mouth portion 53, the flange portion 21 of the ultraviolet irradiation unit 1 is made to abut on the opening side end portion 61 of the joint 51, and the ultraviolet irradiation unit 1 is thereby fixed. For example, the ultraviolet irradiation unit 1 may be fixed to the first mouth portion 53 by an adhesive or welding.

An inflow side flow channel pipe 63 is connected to the second mouth portion 55. The inflow side flow channel pipe 63 is an existing flow channel pipe and is fixed to the second mouth portion 55 by, for example, a screw, an adhesive, welding, or the like. A fluid supply device or the like (not shown) is connected to an upstream side of the inflow side flow channel pipe 63.

An outflow side flow channel pipe 65 is connected to the third mouth portion 57. The outflow side flow channel pipe 65 is an existing passage pipe and is fixed to the third mouth portion 57 by, for example, a screw, an adhesive, welding, or the like. A liquid storage device or the like (not shown) is connected to a downstream side of the outflow side flow channel pipe 65.

The fluid introduced from the fluid supply device into the second mouth portion 55 via the inflow side flow channel pipe 63 is sterilized by ultraviolet rays emitted from the ultraviolet irradiation unit 1 while flowing through the inflow side flow channel pipe 63 and the second mouth portion 55. Subsequently, the sterilized fluid flows to the liquid storage device via the third mouth portion 57 and the outflow side flow channel pipe 65. Thus, the ultraviolet sterilization device 49 can sterilize the fluid with ultraviolet rays.

The flow rate of the fluid may be a flow rate that enables the fluid to be sterilized by the irradiation of ultraviolet rays while the fluid flows through the inflow side flow channel pipe 63 and the second mouth portion 55, and is, for example, 1 L/min to 100 L/min.

The fluid is, for example, gas such as air, grains such as wheat flour or other powders, liquid such as tap water or agricultural water.

As described above, since the ultraviolet irradiation unit 1 comprises the cylindrical casing 3 having an outer diameter dimension that enables the casing to fit within a bore of the first mouth portion 53 of the joint 51, the ultraviolet irradiation unit 1 can easily be connected to the joint 51. For this reason, since the ultraviolet irradiation unit 1 can easily be connected to the inflow side flow channel pipe 63 and the outflow side flow channel pipe 65, which are existing flow channel pipes, with the joint 51 interposed and since no equipment for connection is further required, the costs can also be reduced.

As shown in FIG. 2, in the ultraviolet sterilization device 49, the ultraviolet irradiation unit 1 is provided at the first mouth portion 53, which is the mouth portion facing the direction of flow of the fluid, for the fluid flowing through the joint 51, such that the time to irradiate the fluid with the ultraviolet rays can be made longer and the amount of fluid to be sterilized can be increased.

Figure 3:
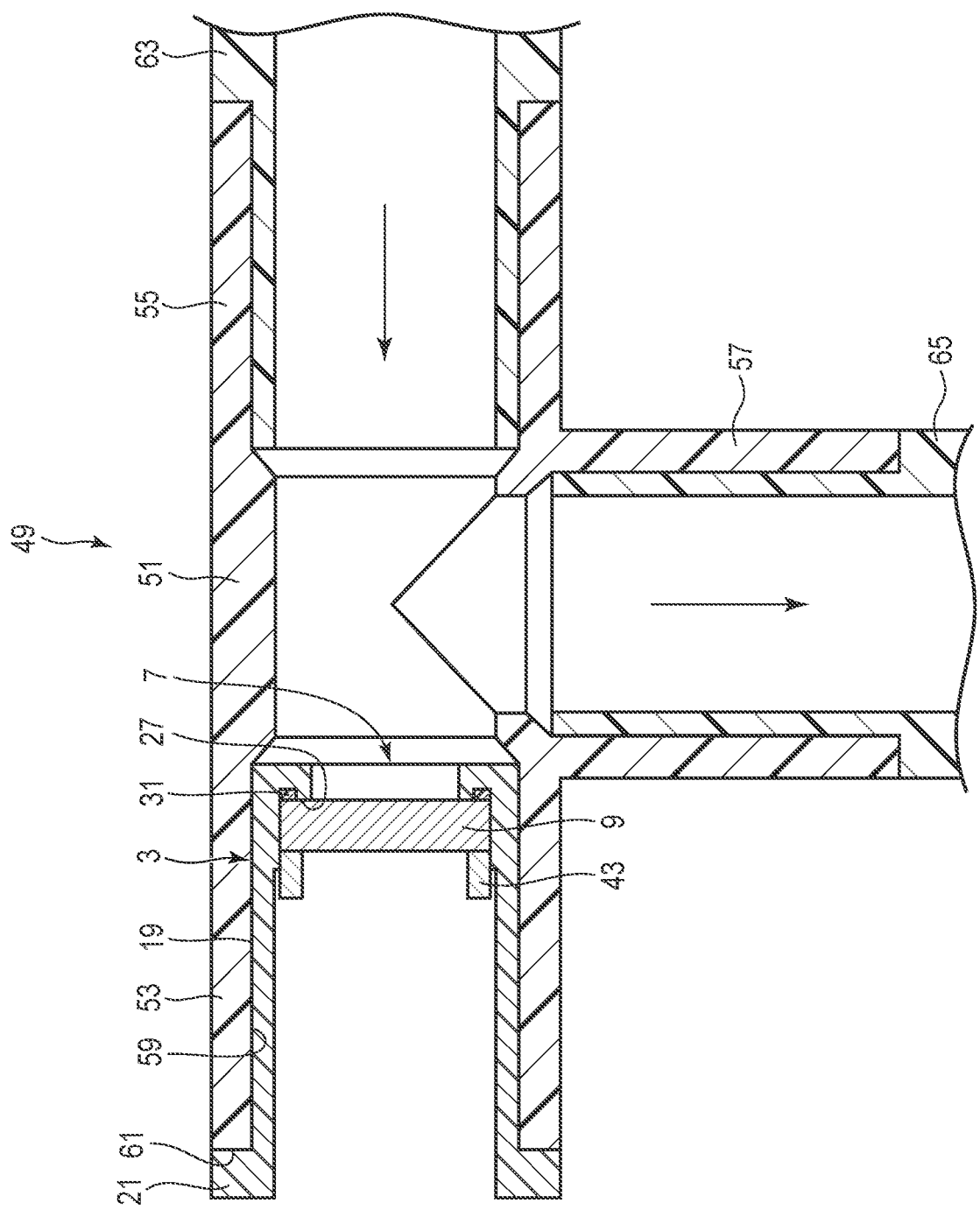
FIG. 3 is a sectional view showing a state in which the ultraviolet irradiation module is removed from the ultraviolet sterilization device shown in FIG. 2.

The ultraviolet sterilization device 49 can be replaced and maintained as described below. As shown in FIG. 3, in the ultraviolet sterilization device 49, only the ultraviolet irradiation module 11 can be removed while leaving the casing 3 of the ultraviolet irradiation unit 1 and the ultraviolet transmitting body 9. Subsequently, a new ultraviolet irradiation module 11 is mounted in the casing 3 of the ultraviolet irradiation unit 1 such that the current ultraviolet irradiation module 11 can be replaced with the new ultraviolet irradiation module 11. For this reason, for the ultraviolet sterilization device 49, only the ultraviolet irradiation module 11 needs to be prepared without preparing another ultraviolet irradiation unit 1, so that the costs can be reduced. In addition, since the ultraviolet transmitting body 9 is sandwiched between the packing 31 and the ultraviolet transmitting body abutting portion 27, and the spacer 43, the fluid can be prevented from leaking to the outside.

Other embodiments of the present invention will be described below. In the embodiments described below, parts having the same advantages as those of the above-described Embodiment 1 are denoted by the same reference numerals, and detailed description will be omitted. In the following descriptions, points mainly different from the Embodiment 1 will be described.

Embodiment 2

An ultraviolet irradiation unit 1 of Embodiment 2 will be described with reference to FIG. 4. The ultraviolet irradiation unit 1 of the Embodiment 2 differs from the ultraviolet irradiation unit 1 of the Embodiment 1 with respect to the only feature of including a reflector 67 instead of the spacer 43.

Figure 4:
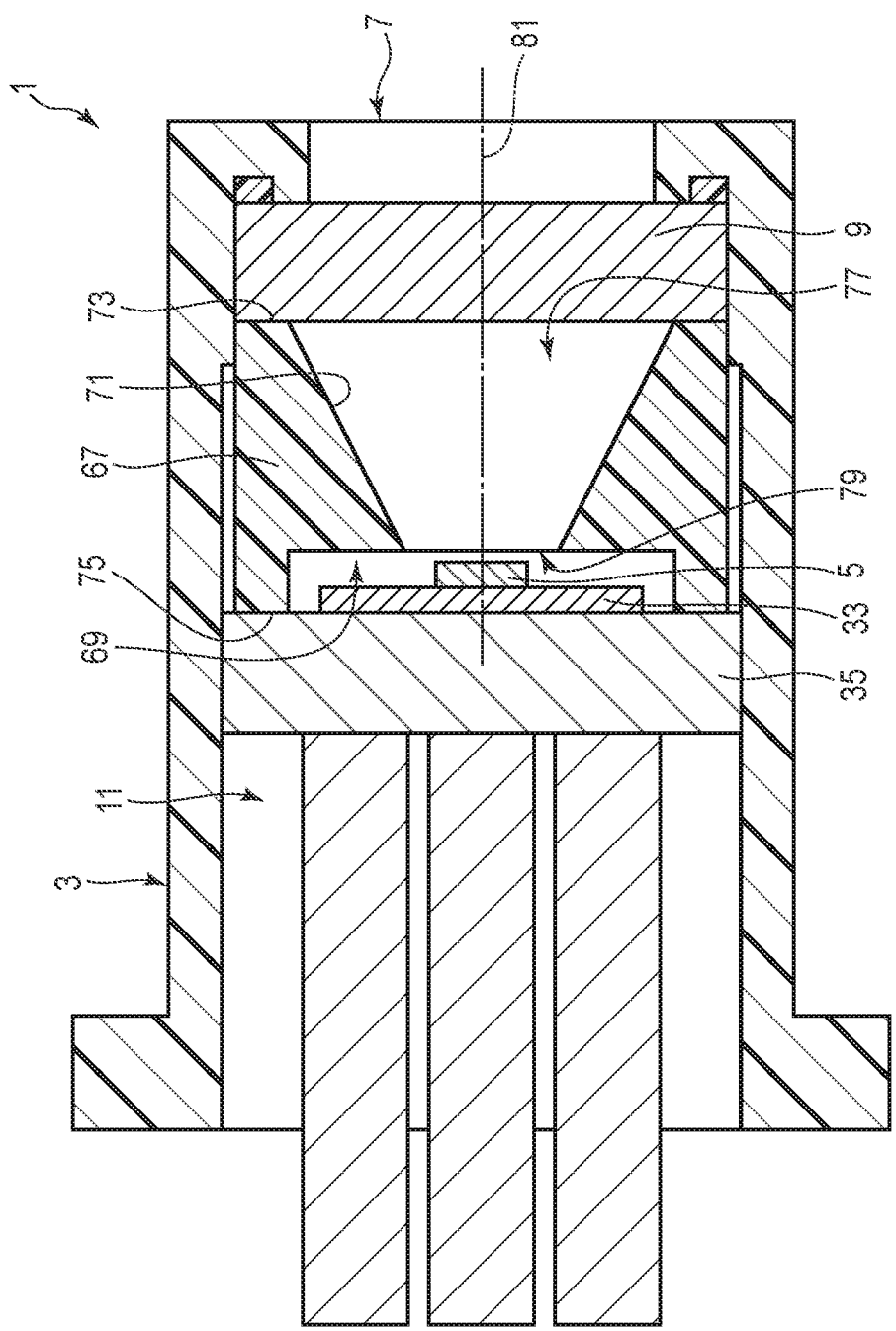
FIG. 4 is a cross-sectional view showing an ultraviolet irradiation unit of Embodiment 2.

As shown in FIG. 4, the ultraviolet irradiation unit 1 of the Embodiment 2 includes the reflector 67 that is in contact with the vicinity of the outer periphery of an ultraviolet transmitting body 9 and is arranged around a light source 5.

The reflector 67 includes a concave portion 69, an ultraviolet reflection surface 71, an ultraviolet emission opening side surface 73, a module insertion opening side surface 75, an ultraviolet emission opening side opening portion 77, and a module insertion opening side opening portion 79.

The reflector 67 reflects part of ultraviolet rays (i.e., ultraviolet rays having a large emission angle), of the ultraviolet rays emitted from the light source 5 toward the ultraviolet transmitting body 9. The reflector 67 is formed of, for example, polycarbonate resin, acrylic resin, cyclic olefin copolymer (COC), glass, or metal, and at least the surface of the ultraviolet reflection surface 71 is mirror-coated with aluminum. The surface of the concave portion 69 may be coated to protect the resin from ultraviolet rays. The coating of the concave portion 69 and the surface of the ultraviolet reflection surface 71 is, for example, aluminum coating by vapor deposition.

The concave portion 69 accommodates the light source 5 of the ultraviolet irradiation module 11 and a substrate 33. A central part of a bottom of the concave portion 69 communicates with the module insertion opening side opening portion 79.

The ultraviolet reflection surface 71 reflects the ultraviolet rays emitted from the light source 5 and directly reaching the surface toward the ultraviolet transmitting body 9. The ultraviolet reflection surface 71 is a rotation target surface with a central axis 81 serving as a rotation axis, and is circularly symmetric in the present embodiment, and has a linear shape with respect to the central axis 81. The ultraviolet reflecting surface 71 may have a convex curved shape or a concave curved shape in the direction of the central axis 81, and may achieve an object of reflecting the ultraviolet rays emitted from the light source 5 toward the ultraviolet transmitting body 9.

The ultraviolet emission opening side surface 73 is in contact with the vicinity of the outer periphery of the ultraviolet transmitting member 9, and the module insertion opening side surface 75 is in contact with the vicinity of the outer periphery of the surface of the base 35 on the ultraviolet emission opening side. The ultraviolet emission opening side surface 73 and the module insertion opening side surface 75 position the reflector 67 such that the central axis 81 passes through the centers of the ultraviolet emission opening side opening portion 77 and the module insertion opening side opening portion 79.

The ultraviolet emission opening side opening portion 77 is larger than the module insertion opening side opening portion 79. The ultraviolet emission opening side opening portion 77 has, for example, a circular shape with a diameter of 16 mm. The module insertion opening side opening portion 79 has, for example, a circular shape with a diameter of 6 mm.

Since the ultraviolet irradiation unit 1 of Embodiment 2 reflects the ultraviolet rays emitted from the light source 5 toward the ultraviolet transmitting body 9, on the ultraviolet reflection surface 71 of the reflector 67, ultraviolet irradiation unit 1 can apply the ultraviolet rays having a high ultraviolet intensity near the center to the outside. For this reason, the ultraviolet irradiation unit 1 of Embodiment 2 can sufficiently sterilize the fluid by irradiating the fluid flowing through the flow channel pipe, i.e., the fluid of a laminar flow which is fast at the center of the pipe and slow on the pipe wall side, with ultraviolet rays having a high ultraviolet intensity in the vicinity of the center, from a position facing the fluid flow.

In addition, the ultraviolet irradiation unit 1 of Embodiment 2 can suppress direct application of ultraviolet rays on the inner wall of the joint and the inner wall of the flow channel pipe and prevent the joint and the flow channel pipe from being deteriorated by the ultraviolet rays.

Embodiment 3

An ultraviolet irradiation unit 1 of Embodiment 3 will be described with reference to FIG. 5. The ultraviolet irradiation unit 1 of Embodiment 3 is different from the ultraviolet irradiation unit 1 of Embodiment 1 with respect to features of including a reflector 67 instead of the spacer 43, including a first condenser lens as the ultraviolet transmitting body, and including no packing 31.

In Embodiment 3, an ultraviolet transmitting body 9 is a first condenser lens, and includes a convex lens surface 83, a flange portion 85, and a leg portion 87. In Embodiment 3, the ultraviolet transmitting body 9 will be described hereinafter as a first condenser lens.

The convex lens surface 83 is arranged so as to face a light source 5 of an ultraviolet irradiation module 11. The convex lens surface 83 is a surface on which the ultraviolet rays emitted from the light source 5 of the ultraviolet irradiation module 11 and directly arriving and the ultraviolet rays reflected on the ultraviolet reflection surface 71 of the reflector 67 and then arriving are made incident. The convex lens surface 83 is circularly symmetric with a central axis 81 serving as a rotation axis. The convex lens surface 83 is formed such that, in a cross section orthogonal to the central axis 81, the diameter of the cross section becomes larger from the light source 5 side toward the joint 51 side.

The flange portion 85 is arranged around the convex lens surface 83. An ultraviolet emission opening side surface 73 of the reflector 67 is in contact with the flange portion 85.

The leg portion 87 is formed so as to extend from the vicinity of an outer periphery of a side surface opposite to the convex lens surface 83 of the flange portion 85 toward the inside of a packing insertion groove 29 of the casing 3. The leg portion 87 is engaged with the packing insertion groove 29 of the casing 3.

The first condenser lens condenses ultraviolet rays emitted from the light source 5 of the ultraviolet irradiation module 11, i.e., ultraviolet rays emitted from the ultraviolet irradiation module 11 and directly reaching the first condenser lens, and ultraviolet rays emitted from the ultraviolet irradiation module 11 and then reflected on the ultraviolet reflection surface 71 of the reflector 67 and reaching the first condenser lens, and causes the ultraviolet rays to be transmitted to the outside.

The ultraviolet irradiation unit 1 of Embodiment 3 can reflect the ultraviolet rays emitted from the light source 5 toward the ultraviolet transmitting body 9, on the ultraviolet reflection surface 71 of the reflector 67, and can condense the ultraviolet rays emitted from the light source 5 of the ultraviolet irradiation module 11 on the first condenser lens which is the ultraviolet transmitting body 9 and apply the ultraviolet rays having a higher ultraviolet intensity in the vicinity to the center toward the outside to cause the ultraviolet rays to be transmitted to the outside. For this reason, the ultraviolet irradiation unit 1 of Embodiment 3 can further sterilize the fluid sufficiently by irradiating the fluid flowing through the flow channel pipe, i.e., the fluid of a laminar flow which is fast at the center of the pipe and slow on the pipe wall side, with ultraviolet rays having a further higher ultraviolet intensity in the vicinity of the center, from a position facing the fluid flow.

In addition, the ultraviolet irradiation unit 1 of Embodiment 3 can further suppress direct application of ultraviolet rays on the inner wall of the joint and the inner wall of the flow channel pipe and further prevent the joint and the flow channel pipe from being deteriorated by the ultraviolet rays.

Embodiment 4

Figure 6:
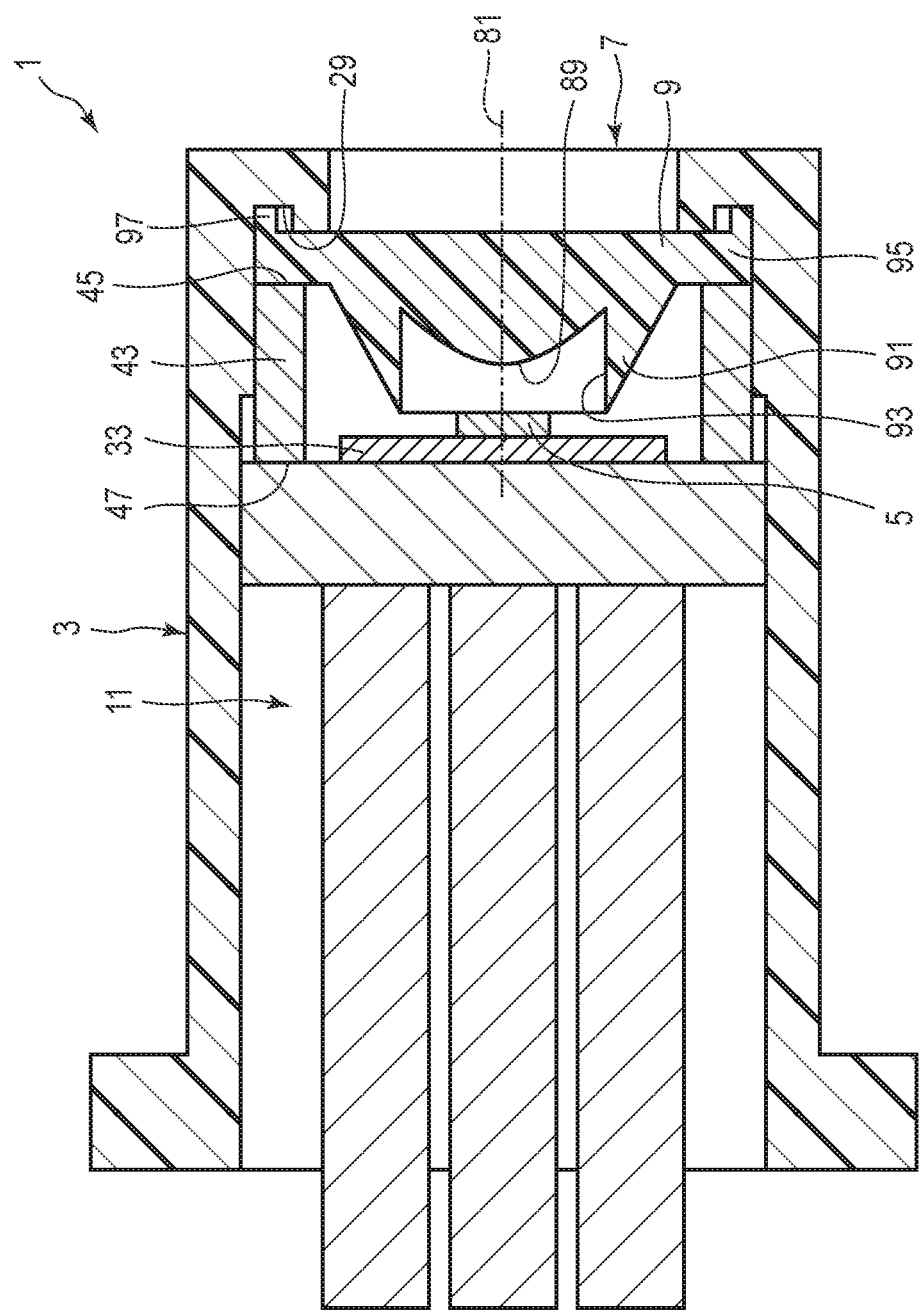
FIG. 6 is a cross-sectional view showing an ultraviolet irradiation unit of Embodiment 4.

An ultraviolet irradiation unit 1 of Embodiment 4 will be described with reference to FIG. 6. The ultraviolet irradiation unit 1 of Embodiment 4 is different from the ultraviolet irradiation unit 1 of Embodiment 1 with respect to a feature of including a second condenser lens as an ultraviolet transmitting body 9.

In Embodiment 4, the ultraviolet transmitting body 9 is a second condenser lens, and includes a convex lens surface 89, a protruding portion 91, an ultraviolet incident surface 93, a flange portion 95, and a leg portion 97. In Embodiment 4, the ultraviolet transmitting body 9 will be described hereinafter as a second condenser lens.

The convex lens surface 89 is arranged so as to face a light source 5 of an ultraviolet irradiation module 11. The convex lens surface 89 is a surface on which ultraviolet rays having a small emission angle, of the ultraviolet rays emitted from the light source 5 of the ultraviolet irradiation module 11, are made incident. The convex lens surface 89 is circularly symmetric with a central axis 81 serving as a rotation axis. The convex lens surface 89 is formed such that, in a cross section orthogonal to the central axis 81, the diameter of the cross section becomes larger from the light source 5 side toward an ultraviolet emission opening 7 side.

The projecting portion 91 extends from the periphery of the convex lens surface 89 toward the ultraviolet irradiation module 11 side and is then linearly inclined from the central axis 81 side toward the outer periphery.

The ultraviolet incident surface 93 is a surface on the side of the central axis 81 of the protruding portion 91 and is a surface on which ultraviolet rays having a large emission angle, of the ultraviolet rays emitted from the light source 5 of the ultraviolet irradiation module 11, are made incident.

The flange portion 85 is arranged around the protruding portion 91. One end 45 of a spacer 43 is in contact with the surface of the flange portion 95 on the ultraviolet irradiation module 11 side.

The leg portion 97 is formed so as to extend from the vicinity of an outer periphery of a side surface opposite to the convex lens surface 89 of the flange portion 95 toward the inside of a packing insertion groove 29 of the casing 3. The leg portion 97 is engaged with the packing insertion groove 29 of the casing 3.

The second condenser lens condenses ultraviolet rays emitted from the light source 5 of the ultraviolet irradiation module 11, i.e., ultraviolet rays emitted from the ultraviolet irradiation module 11 and reaching the convex lens surface 89, and ultraviolet rays emitted from the ultraviolet irradiation module 11 and reaching the ultraviolet incident surface 93, and causes the ultraviolet rays to be transmitted to the outside.

The ultraviolet irradiation unit 1 of Embodiment 4 can condense the ultraviolet rays emitted from the light source 5 of the ultraviolet irradiation module 11 on the second condenser lens, which is the ultraviolet transmitting body 9, and apply the ultraviolet rays having a higher ultraviolet intensity in the vicinity to the center toward the outside to cause the ultraviolet rays to be transmitted to the outside. For this reason, the ultraviolet irradiation unit 1 of Embodiment 4 can sterilize the fluid by irradiating the fluid flowing through the flow channel pipe, i.e., the fluid of a laminar flow which is fast at the center of the pipe and slow on the pipe wall side, with ultraviolet rays having a high ultraviolet intensity in the vicinity of the center, from a position facing the fluid flow.

In addition, the ultraviolet irradiation unit 1 of Embodiment 4 can suppress direct application of ultraviolet rays on the inner wall of the joint and the inner wall of the flow channel pipe and prevent the joint and the flow channel pipe from being deteriorated by the ultraviolet rays.

Figure 7:
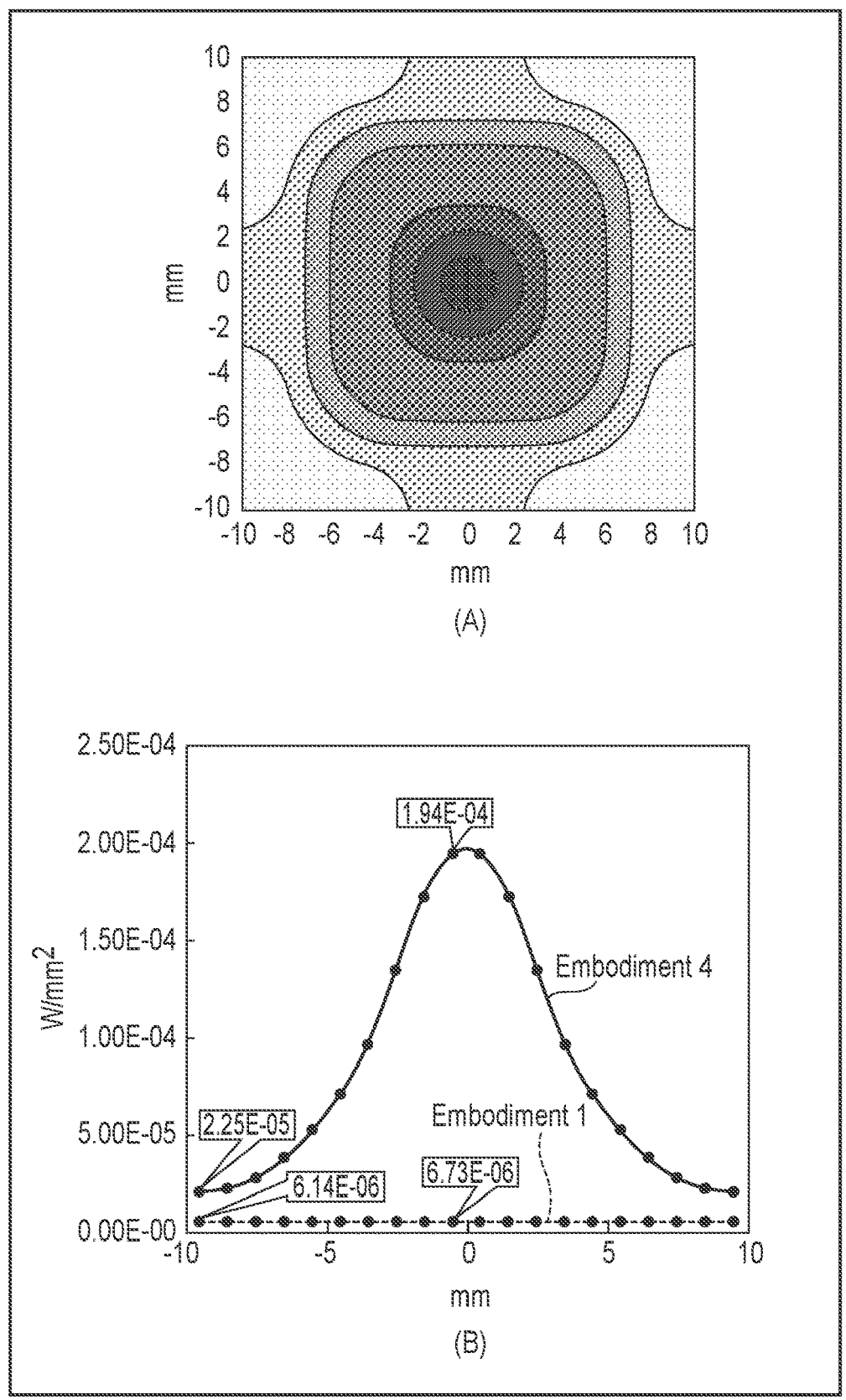
FIG. 7, part (A) is a distribution graph of an ultraviolet irradiation intensity of the ultraviolet irradiation unit of Embodiment 4 at a position separate from the upper surface of a casing in 28 mm, and part (B) is a graph showing the ultraviolet irradiation intensity of the ultraviolet irradiation unit at a position separate from the upper surface of the casing in 28 mm.

An ultraviolet irradiation unit 1 of Embodiment 4 will be described with reference to FIG. 7. As shown in (A) and (B) of FIG. 7, it can be understood that, at 28 mm from an upper surface of the casing 3, the ultraviolet irradiation unit 1 of Embodiment 4 has a strength of 1.94 E−4 W/mm$^2$ or more in a range of a linear distance of approximately 1 mm from the center, and has a strength of approximately 2.25 E−5 W/mm$^2$ at a position separated by a linear distance of approximately 10 mm from the center. In contrast, it can be understood that, at 28 mm from the upper surface of the casing 3, the ultraviolet irradiation unit 1 of Embodiment 1 has a strength of approximately 6.73 E−6 W/mm² at a position separated by a linear distance of approximately 1 mm from the center, and has a strength of approximately 6.14 E−6 W/mm² at a position separated by a linear distance of approximately 10 mm from the center. Therefore, since the ultraviolet irradiation unit 1 of Embodiment 4 comprises the second condenser lens as the ultraviolet transmitting body 9, and condenses the ultraviolet rays emitted from the light source 5 of the ultraviolet irradiation module 11 on the second condenser lens to cause the ultraviolet rays to be transmitted to the outside, the ultraviolet irradiation unit 1 can apply the ultraviolet rays having a high ultraviolet intensity in the vicinity to the center.

Embodiment 5

An ultraviolet irradiation unit 1 of Embodiment 5 will be described with reference to FIG. 1. The ultraviolet irradiation unit 1 of Embodiment 5 comprises a casing 3 formed of a material having a high thermal conductivity as a casing. The material having a high thermal conductivity is, for example, PPS containing carbon black, aluminum, or the like.

Since the ultraviolet irradiation unit 1 of Embodiment 5 comprises the casing 3 formed of a material having a high thermal conductivity, the heat generated from the light source 5 moves to each of heat radiating plates 37 and the casing 3 through a substrate 33 and a base 35. The heat moving to each of the heat radiating plates 37 is released into the atmosphere, and the heat moving to the casing 3 moves from a fluid contact portion 25 into the fluid. For this reason, since the ultraviolet irradiation unit 1 of Embodiment 5 improves heat radiation by releasing the heat of the light source 5 into the atmosphere or moving the heat into the fluid, the unit can suppress or prevent the light source 5 becoming a high temperature state (in which, for example, the temperature of the substrate adjacent to the light source 5 is 65° C. or higher) at the time of applying the ultraviolet rays, and the premature deterioration of the light source 5.

Figure 8:
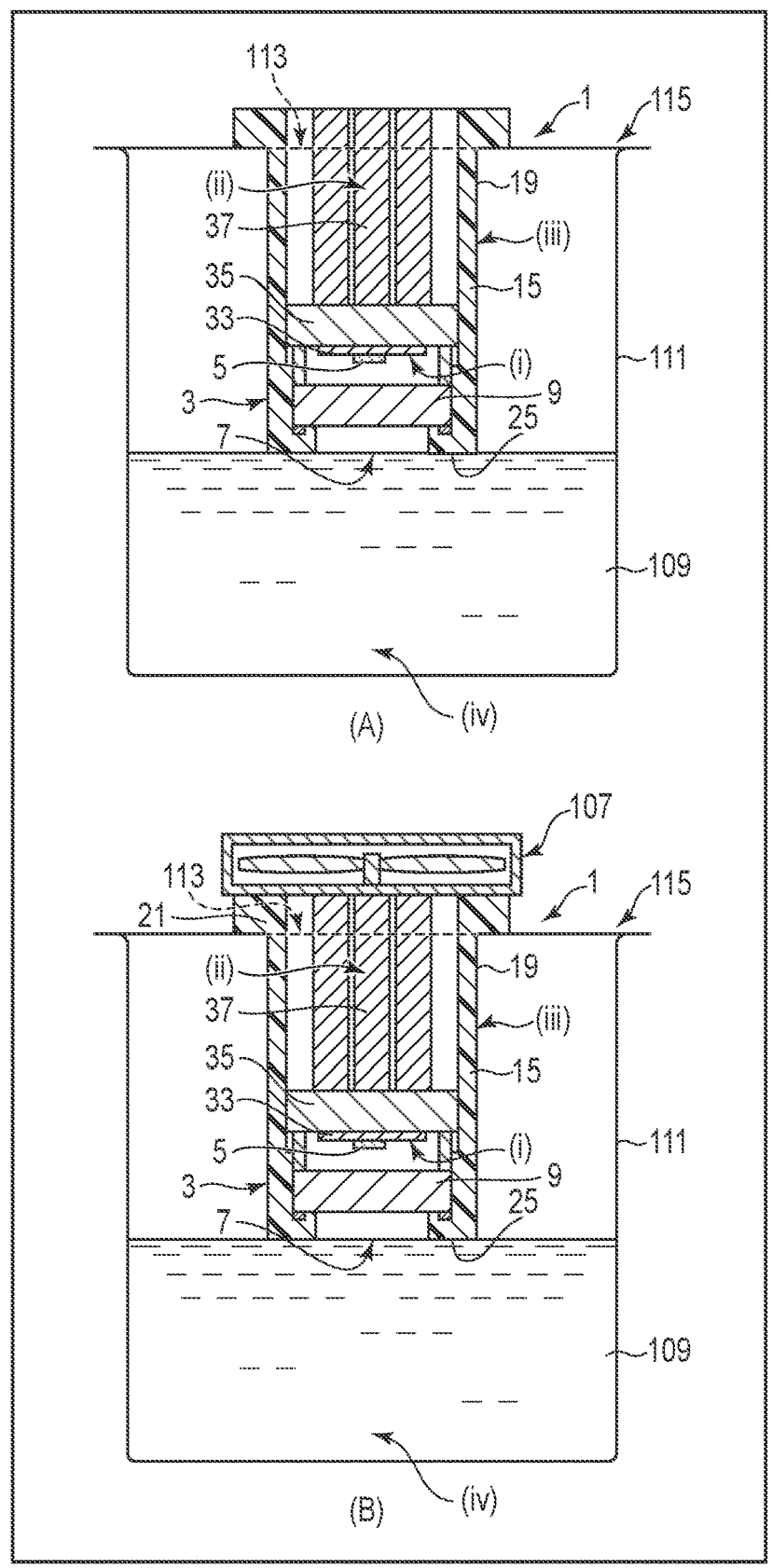
FIG. 8, part (A) is a diagram showing a situation of a heat radiation test of the ultraviolet irradiation unit of Examples 1 to 3, and part (B) is a diagram showing a situation of a heat radiation test of the ultraviolet irradiation unit of Example 4.
Figure 9:
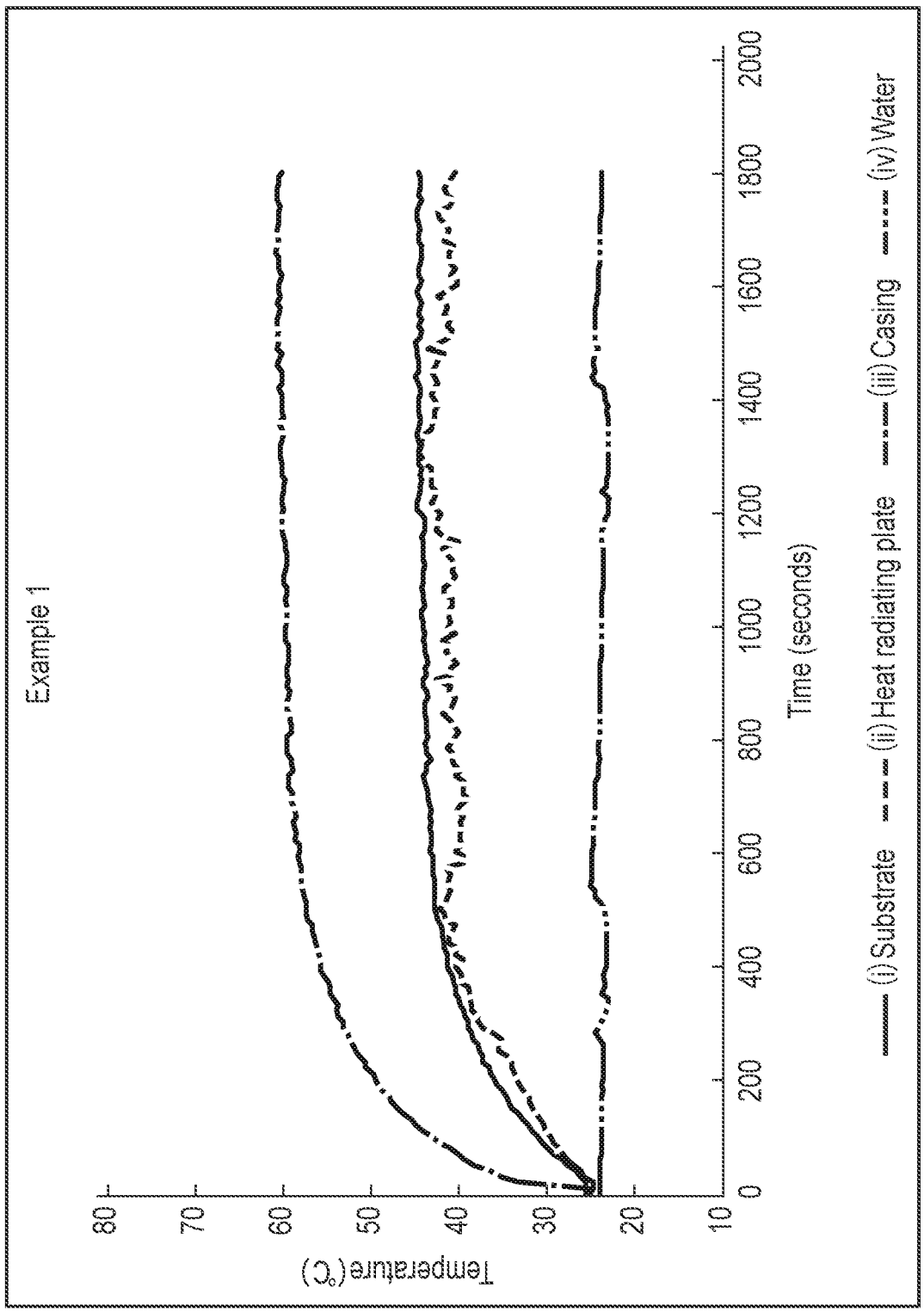
FIG. 9 is a graph showing a relationship between each part of the ultraviolet irradiation unit of Example 1 and a water temperature and time.
Figure 10:
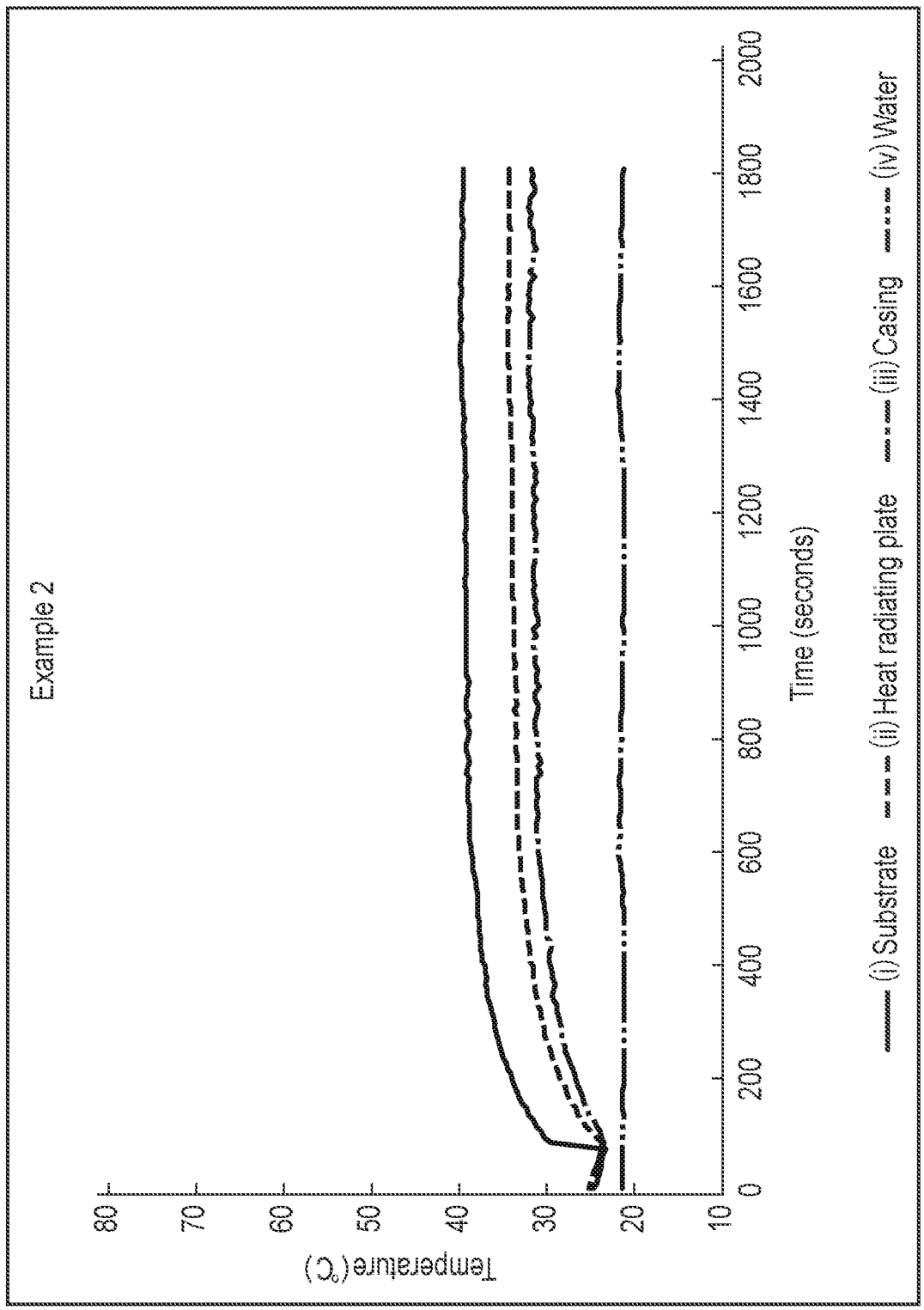
FIG. 10 is a graph showing a relationship between each part of the ultraviolet irradiation unit of Example 2 and a water temperature and time.
Figure 11:
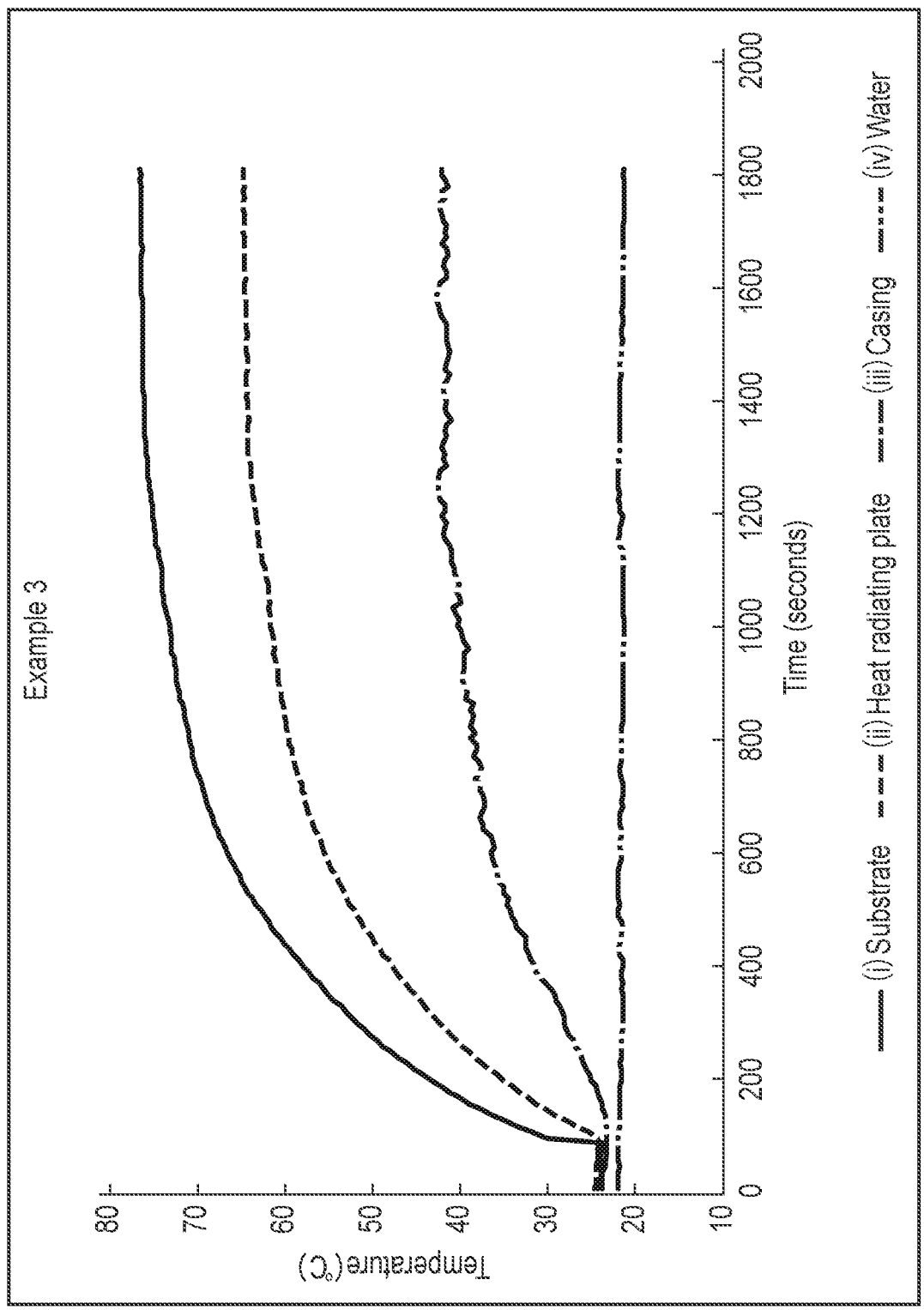
FIG. 11 is a graph showing a relationship between each part of the ultraviolet irradiation unit of Example 3 and a water temperature and time.
Figure 12:
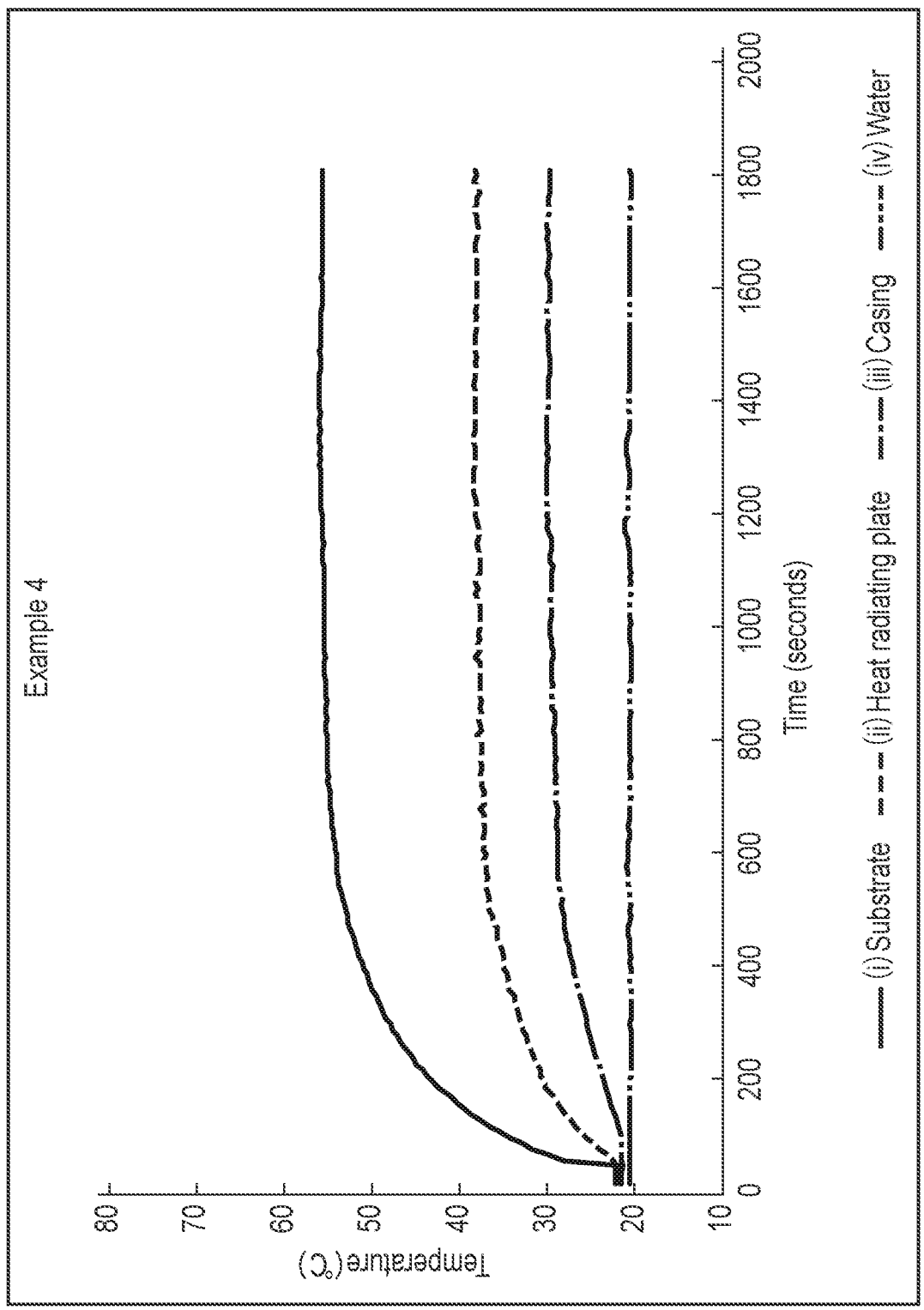
FIG. 12 is a graph showing a relationship between each part of the ultraviolet irradiation unit of Example 4 and a water temperature and time.

A heat radiation test as shown in FIG. 8 was conducted in order to evaluate the heat radiation of the ultraviolet irradiation unit 1 of Embodiment 5. First, ultraviolet irradiation units of Examples 1 to 4 mentioned below were prepared as the ultraviolet irradiation units used for the heat dissipation test.

Example 1

Ultraviolet irradiation unit 1 comprising the casing 3 formed of PPS containing carbon black (Embodiment 5)

Example 2

Ultraviolet irradiation unit 1 comprising the casing 3 formed of aluminum (Embodiment 5)

Example 3

Ultraviolet irradiation unit 1 comprising the casing 3 formed of vinyl chloride

Example 4

Ultraviolet irradiation unit 1 comprising the casing 3 formed of vinyl chloride and a fan 107, which is a heat radiation device, attached to the flange portion 21 of the casing 3

Next, four sets of beakers 111 containing water 109 at room temperature and plates 115 including holes 113 having the same diameter as the outer diameter dimension of the casing body 15 were prepared. After that, a thermocouple (not shown) for temperature measurement was attached to each of the surface of the substrate 33 on the light source 5 side (point i), the surface of the heat radiation plate 37 (point ii), and the surface of the outer wall 19 of the casing body 15 of the casing 3 (point iii), in each of the ultraviolet irradiation units 1 of Examples 1 to 3. Next, a thermocouple (not shown) for temperature measurement was also arranged in water 109 (point iv) of each beaker 111. After that, the casing body 15 of each ultraviolet irradiation unit 1 to which the thermocouple was attached was inserted into the hole 113 of the plate 115 such that the fluid contact portion 25 of the casing 3 was brought into contact with the surface of the water, and each plate 115 was arranged on the opening of the beaker 111 ((A) of FIG. 8).

Next, thermocouples (not shown) for temperature measurement were attached to the surface of the substrate 33 on the light source 5 side (point i), the surface of the heat radiation plate 37 (point ii), and the surface of the outer wall 19 of the casing body 15 of the casing 3 (point iii), in the ultraviolet irradiation unit 1 of Example 4. After that, a thermocouple (not shown) for temperature measurement was also arranged in the water 109 (point iv) of each beaker 111. Next, the casing body 15 of the ultraviolet irradiation unit 1 to which the thermocouple was attached was inserted into the hole 113 of the plate 115 such that the fluid contact portion 25 of the casing 3 was brought into contact with the surface of water, and the plate 115 was arranged on the opening of the beaker 111 and the preparation was completed ((B) of FIG. 8).

Then, the heat radiation test was started by applying ultraviolet rays from the light source 5 of each ultraviolet irradiation unit 1 of Examples 1 to 4. As the heat radiation test, the temperatures of points i to iii and water (point iv) of each ultraviolet irradiation unit 1 of Examples 1 to 4 were measured at 10 second intervals from the start of ultraviolet irradiation (0 seconds) to 1,800 seconds. The results are shown in FIGS. 9 to 12. In addition, Table 1 shows the temperatures of points i to iii and water (point iv) of each ultraviolet irradiation unit 1 of Examples 1 to 4 after 1,800 seconds of the ultraviolet irradiation.

TABLE 1

| | Temperature[° C.] | | | |
|---|---|---|---|---|
| Examples | Base | Heat radiating plate | Casing | Water |
| 1 | 60.1 | 40.3 | 44.4 | 23.6 |
| 2 | 39.8 | 34.5 | 32.0 | 21.6 |
| 3 | 79.3 | 66.9 | 43.2 | 21.3 |
| 4 | 58.1 | 39.8 | 31.0 | 21.5 |

The heat radiation of the ultraviolet irradiation unit 1 of Embodiment 5 will be described with reference to Table 1. As shown in Table 1, it can be understood that the substrate temperature of the ultraviolet irradiation unit 1 of Example 1 is 60.1° C., the substrate temperature of the ultraviolet irradiation unit 1 of Example 2 is 39.8° C., and the substrate temperature of the ultraviolet irradiation unit 1 of Example 3 is 79.3° C. Therefore, it can be understood that since the ultraviolet irradiation units 1 of Examples 1 and 2 that are Embodiment 5 comprise the casings 3 formed of the material having a high thermal conductivity, the heat of the light source 5 is moved to the heat radiating plates 37 and the casing 3 through the substrate 33 and the base 35, the heat moved to the casing 3 is moved from the fluid contact portion 25 into the water, and the heat radiation performance is thereby improved.

In addition, as shown in Table 1, it can be understood that the substrate temperature of the ultraviolet irradiation unit 1 of Example 1 is 60.1° C., the substrate temperature of the ultraviolet irradiation unit 1 of Example 3 is 79.3° C., and the substrate temperature of the ultraviolet irradiation unit 1 of Example 4 is 58.1° C. It can be understood from this that the ultraviolet irradiation unit 1 of Example 1, which is Embodiment 5, cools the temperature of the substrate to the same extent as the ultraviolet irradiation unit 1 of Example 4 comprising the heat radiation device. Therefore, since the ultraviolet irradiation unit 1 of Example 1, which is Embodiment 5, comprises the casing 3 formed of a material having a high thermal conductivity, a heat radiation device such as the fan 107 is not required, the costs for the radiation device can be reduced and the ultraviolet irradiation unit can be downsized.

Furthermore, as shown in Table 1, it can be understood that the substrate temperature of the ultraviolet irradiation unit 1 of Example 2 is 39.8° C., the substrate temperature of the ultraviolet irradiation unit 1 of Example 3 is 79.3° C., and the substrate temperature of the ultraviolet irradiation unit 1 of Example 4 is 58.1° C. It can be understood from this that the ultraviolet irradiation unit 1 of Example 2, which is Embodiment 5, cools the temperature of the substrate by 18° C. or more than the ultraviolet irradiation unit 1 of Example 4 comprising the heat radiation device. Therefore, since the ultraviolet irradiation unit 1 of Example 2, which is Embodiment 5, comprises the casing 3 formed of a material having a high thermal conductivity, a heat radiation device such as the fan 107 is not required, the costs for the radiation device can be reduced and the ultraviolet irradiation unit can be downsized.

Embodiment 6

Figure 13:
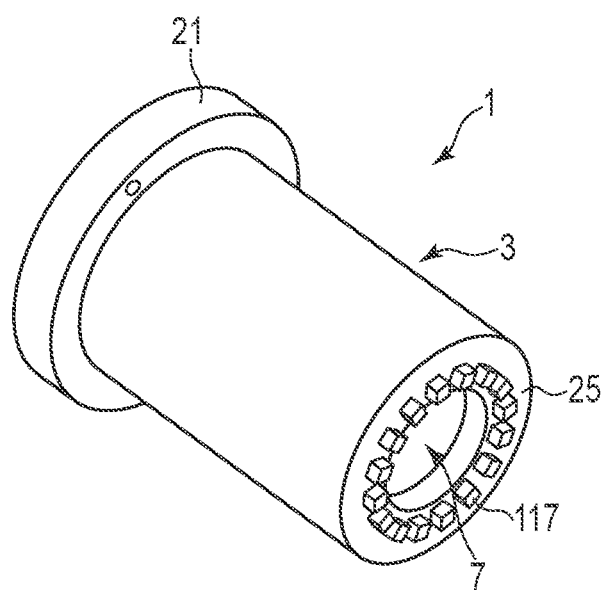
FIG. 13 is a perspective view showing an ultraviolet irradiation unit of Embodiment 6.

An ultraviolet irradiation unit 1 of Embodiment 6 will be described with reference to FIG. 13. The ultraviolet irradiation unit 1 of Embodiment 6 is different from the ultraviolet irradiation unit 1 of Embodiment 1 with respect to a feature of including a plurality of heat radiating protruding portions 117 having a rectangular parallelepiped shape, which protrude toward the direction of ultraviolet irradiation from the fluid contact portion 25 of the housing 3 and which are provided in the circumferential direction and spaced apart at intervals.

The plurality of heat radiating protruding portions 117 having a rectangular parallelepiped shape protrude from the fluid contact portion 25 of the casing 3 toward the ultraviolet irradiation direction, and increase the surface area of the fluid contact portion 25 in contact with the fluid. The plurality of heat radiating protruding portions 117 are formed of the same material as the casing 3 and are formed together with the casing 3 by, for example, integral molding.

Figure 14:
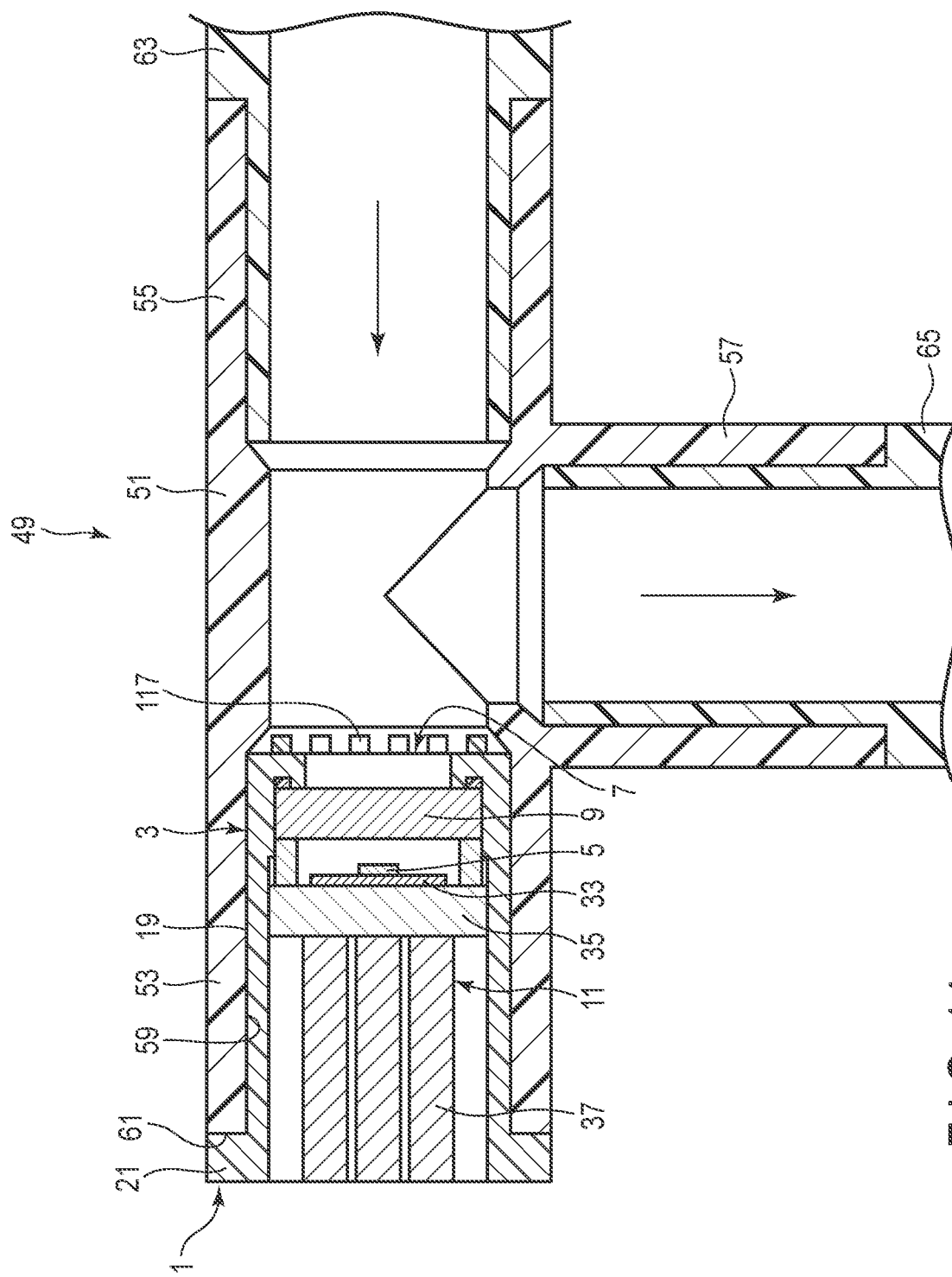
FIG. 14 is a cross-sectional view showing an ultraviolet sterilization device comprising an ultraviolet irradiation unit of Embodiment 6.

As shown in FIG. 14, in the ultraviolet irradiation unit 1 of Embodiment 6, the plurality of heat radiating protruding portions 117 having a rectangular parallelepiped shape are inserted into the first mouth portion 53 of the joint 51 so as to be directed toward the second mouth portion 55 of the joint 51. Since the ultraviolet irradiation unit 1 of Embodiment 6 includes the plurality of heat radiating protruding portions 117 having a rectangular parallelepiped shape, heat generated from the light source 5 is moved to each of the heat radiating plates 37 and the casing 3 via the substrate 33 and the base 35, and the heat moving to the casing 3 moves from the plurality of heat radiating protruding portions 117 having a rectangular parallelepiped shape into the fluid. For this reason, the ultraviolet irradiation unit 1 of Embodiment 6 can suppress or prevent the light source 5 becoming in a high temperature state and the premature deterioration of the light source 5 by moving the heat of the light source 5 into the fluid. Furthermore, since the ultraviolet irradiation unit 1 of Embodiment 6 includes the plurality of heat radiating protruding portions 117 having a rectangular parallelepiped shape, the heat radiation device is not required, the costs for the heat radiation device can be reduced, and the ultraviolet irradiation unit can be downsized.

Embodiment 7

Figure 15:
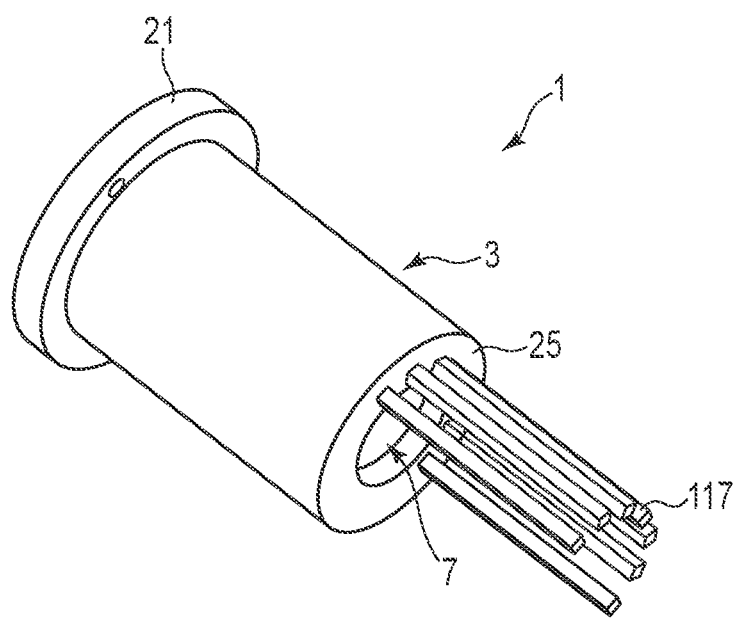
FIG. 15 is a perspective view showing an ultraviolet irradiation unit of Embodiment 7.

An ultraviolet irradiation unit 1 of Embodiment 7 will be described with reference to FIG. 15. The ultraviolet irradiation unit 1 of Embodiment 7 is different from the ultraviolet irradiation unit 1 of Embodiment 1 with respect to a feature of including a plurality of heat radiating protruding portions 117 having a rectangular column shape, which protrude from a fluid contact portion 25 of a housing 3 toward the direction of ultraviolet irradiation in a long length and which are provided in a half circumferential region of the fluid contact portion 25 in the circumferential direction and spaced apart at intervals.

The plurality of heat radiating protruding portions 117 having a rectangular column shape protrude from the fluid contact portion 25 of the casing 3 toward the ultraviolet irradiation direction, and increase the surface area of the fluid contact portion 25 in contact with the fluid. The plurality of heat radiating protruding portions 117 are formed of the same material as the casing 3 and are formed together with the casing 3 by, for example, integral molding.

Figure 16:
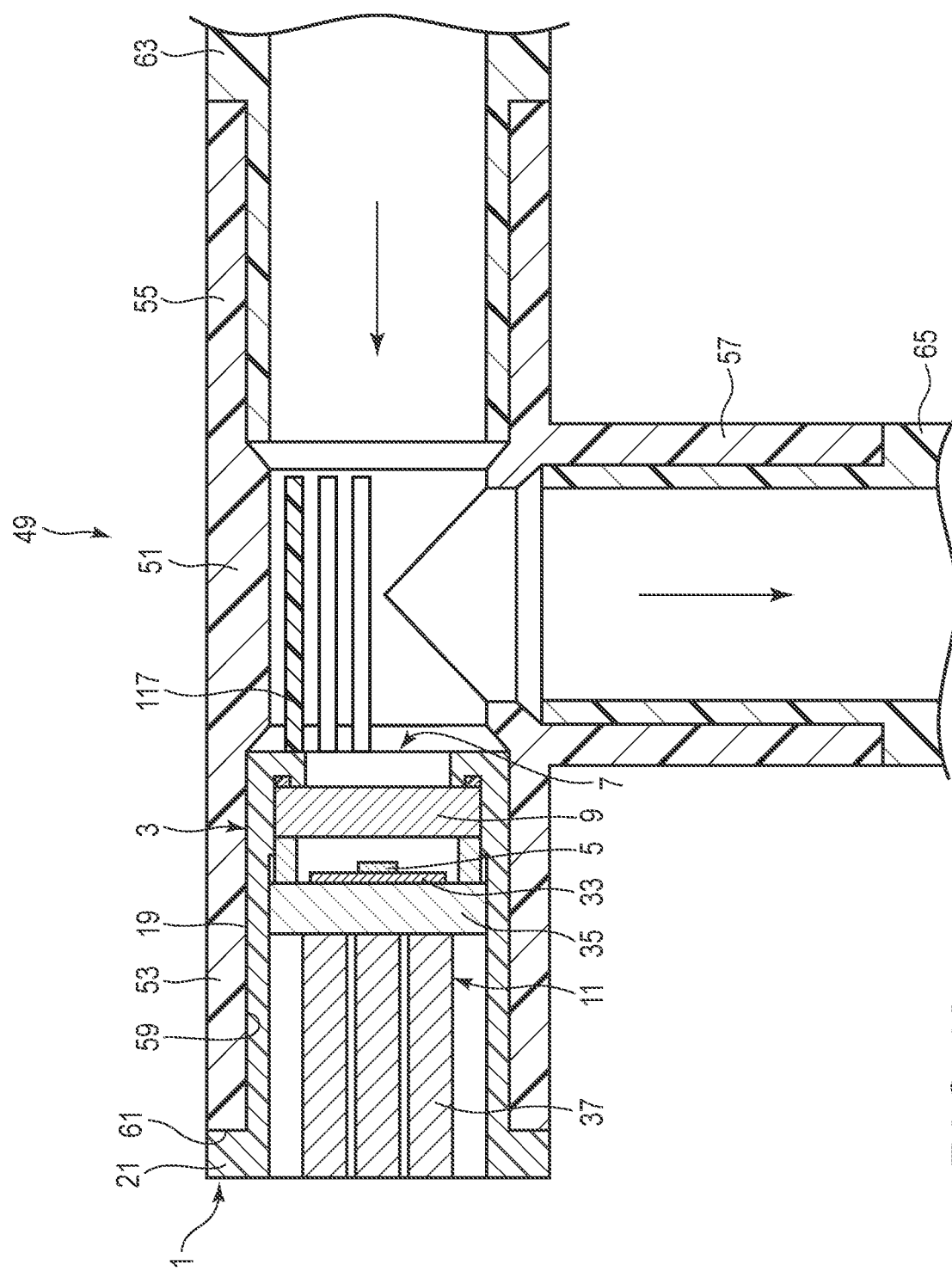
FIG. 16 is a cross-sectional view showing an ultraviolet sterilization device comprising an ultraviolet irradiation unit of Embodiment 7.

As shown in FIG. 16, in the ultraviolet irradiation unit 1 of Embodiment 7, the plurality of heat radiating protruding portions 117 having a columnar shape are inserted into a first mouth portion 53 of a joint 51 so as to be located on a side opposite to a third mouth portion 57 of the joint 51. For this reason, the ultraviolet irradiation unit 1 of Embodiment 7 does not hinder the flow of the fluid from a second mouth portion 55 to the third mouth portion 57.

In addition, since the ultraviolet irradiation unit 1 of Embodiment 7 includes the plurality of heat radiating protruding portions 117 having a rectangular column shape, heat generated from the light source 5 is moved to each of the heat radiating plates 37 and the casing 3 via the substrate 33 and the base 35, and the heat moving to the casing 3 moves from the plurality of heat radiating protruding portions 117 having a columnar shape into the fluid. For this reason, the ultraviolet irradiation unit 1 of Embodiment 7 can suppress or prevent the light source 5 becoming in a high temperature state and the premature deterioration of the light source 5 by moving the heat of the light source 5 into the fluid. Furthermore, since the ultraviolet irradiation unit 1 of Embodiment 7 includes the plurality of heat radiating protruding portions 117 having a columnar shape, the heat radiation device is not required, the costs for the heat radiation device can be reduced, and the ultraviolet irradiation unit can be downsized.

Embodiment 8

Figure 17:
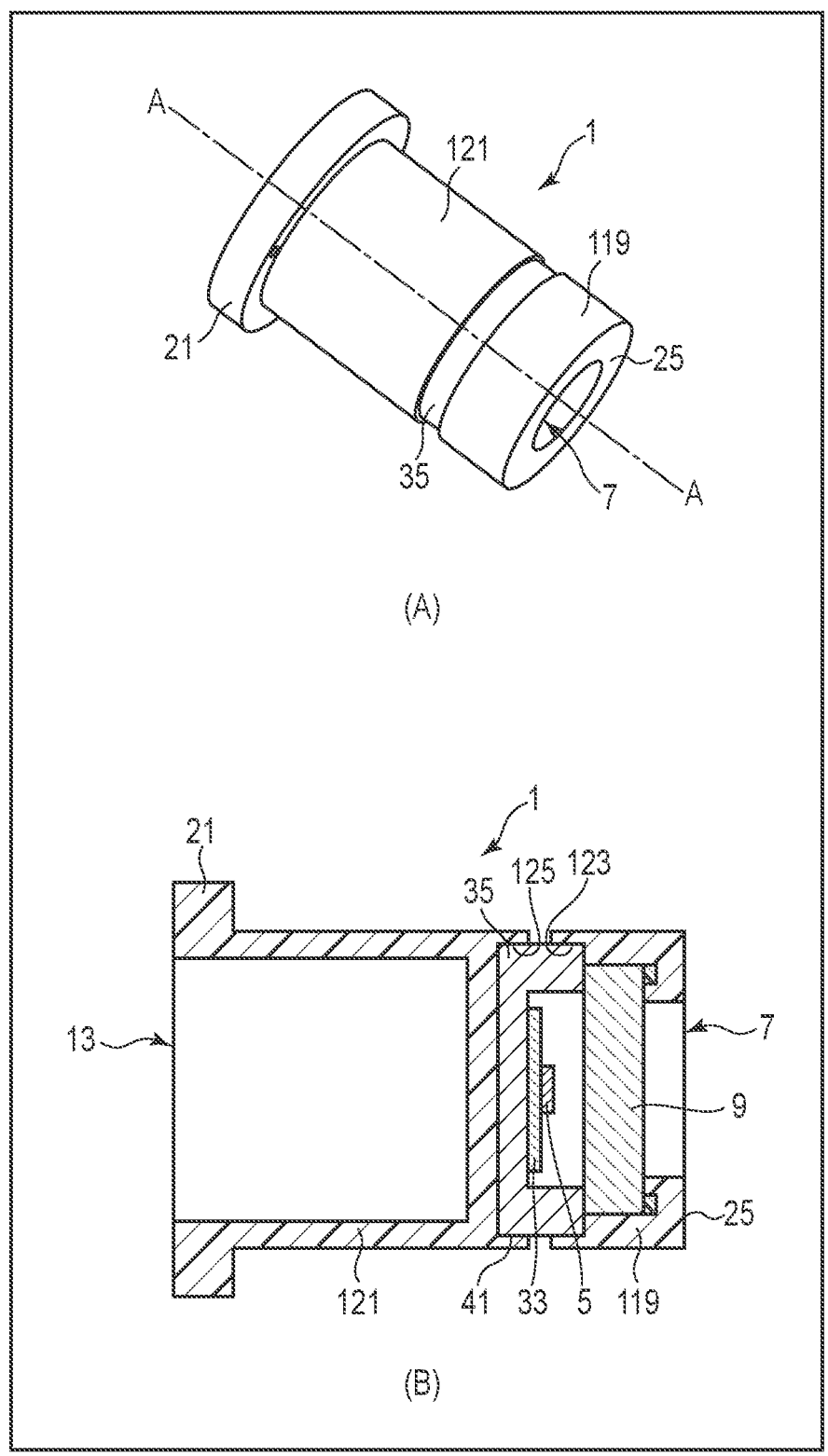
FIG. 17, part (A) is a perspective view showing an ultraviolet irradiation unit of Embodiment 8, and part (B) is a diagram showing a cross section of the ultraviolet irradiation unit of part (A) taken along line A-A.

An ultraviolet irradiation unit 1 of Embodiment 8 will be described with reference to FIG. 17. The ultraviolet irradiation unit 1 of Embodiment 8 is different from the ultraviolet irradiation unit 1 of Embodiment 1 with respect to features that a casing 3 is divided into an ultraviolet emission opening side casing 119 and an anti-ultraviolet emission opening side casing 121, that a base 35 is formed integrally with a spacer 43, that the base 35 is screwed to the ultraviolet emission opening side casing 119 and the anti-ultraviolet emission opening side casing 121 to connect the casing, and that an ultraviolet irradiation module 11 does not include a heat radiating body 39.

The ultraviolet emission opening side casing 119 is provided with a thread groove (not shown) that is screwed into a side wall 41 of the base 35 on an inner wall 125 on a module insertion opening 13 side. The ultraviolet emission opening side casing 119 is formed of, for example, a resin material containing carbon black or a material having a high thermal conductivity such as aluminum (Al).

The anti-ultraviolet emission opening side casing 121 is provided with a thread groove (not shown) that is screwed into the side wall 41 of the base 35 on the inner wall 125 on the ultraviolet emission opening 7 side. The anti-ultraviolet emission opening side casing 121 may be formed of, for example, the same material as the ultraviolet emission opening side casing 119 to be described later or may be formed of a different material therefrom.

The base 35 is formed integrally with the spacer 43, and the screw grooves (not shown) that are screwed into the inner wall 123 of the ultraviolet emission opening side casing 119 and the inner wall 125 of the anti-ultraviolet emission opening side casing 121, respectively, are provided on the side wall 41.

As shown in FIG. 18, in the ultraviolet irradiation unit 1 of Embodiment 8, the casing is divided into the ultraviolet emission opening side casing 119 and the anti-ultraviolet emission opening side casing 121, heat generated from the light source 5 is moved to the ultraviolet emission opening side casing 119 formed of a material having a high thermal conductivity as a heat radiation portion, via a substrate 33 and the base 35, and the heat moved to the ultraviolet emission opening side casing 119 is moved from a fluid contact portion 25 into the fluid. For this reason, the ultraviolet irradiation unit 1 of Embodiment 8 can suppress or prevent the light source 5 becoming in a high temperature state and the premature deterioration of the light source 5 by moving the heat of the light source 5 into the fluid. In the ultraviolet irradiation unit 1 of Embodiment 8, when the anti-ultraviolet emission opening side casing 121 is formed of a material having a high thermal conductivity, heat can be radiated into the atmosphere, but the ultraviolet emission opening side casing 119 and the anti-ultraviolet emission opening side casing 121 do not need to be formed of the same material. When the material having a high thermal conductivity is expensive, only the anti-ultraviolet emission opening side casing 121 is formed of an inexpensive material such as vinyl chloride and the costs can be thereby reduced. Furthermore, since the ultraviolet irradiation unit 1 of Embodiment 8 does not include a heat radiating body 39, the costs for the heat radiating body 39 can be reduced and the ultraviolet irradiation unit can be downsized.

Embodiment 9

Figure 19:
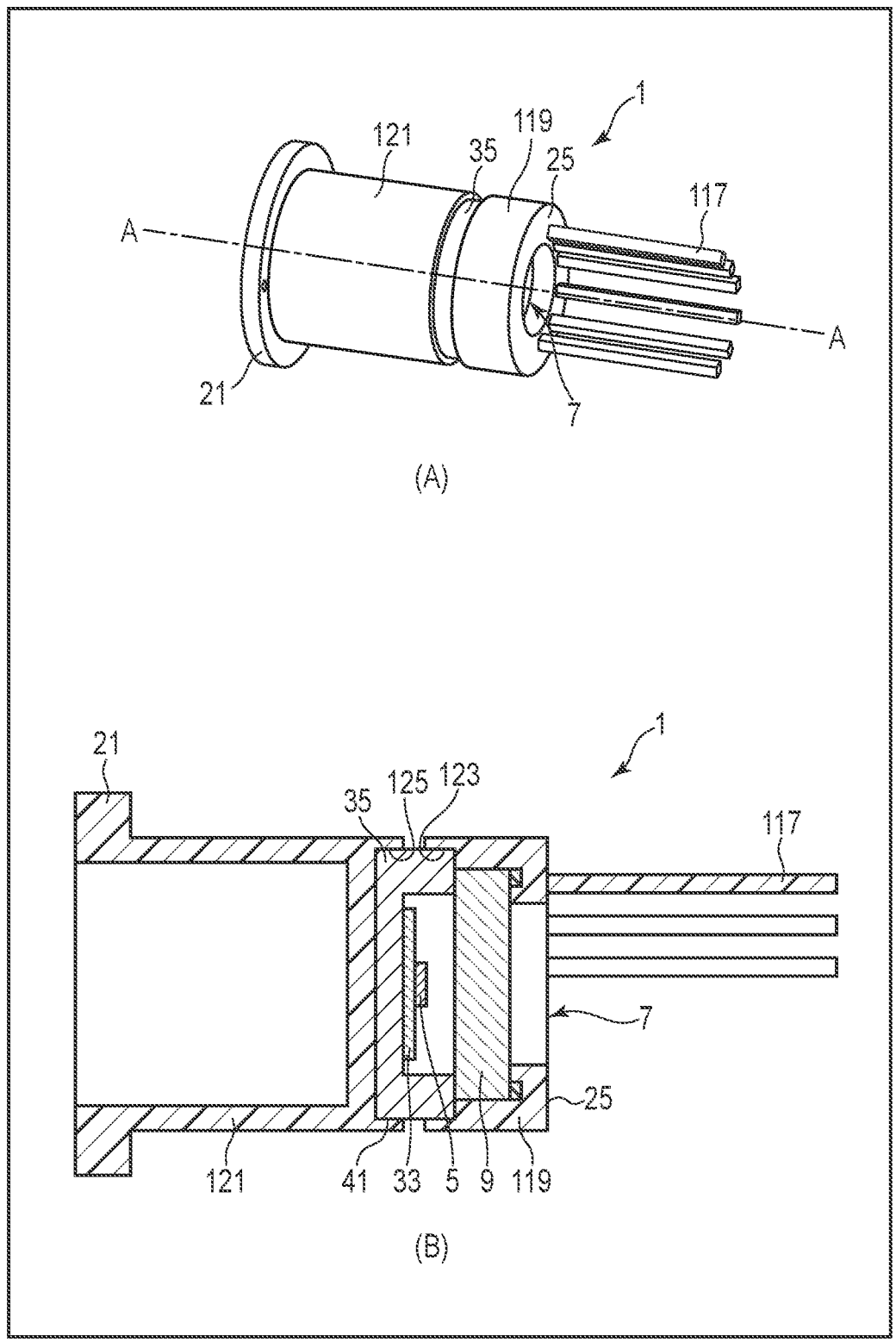
FIG. 19, part (A) is a perspective view showing an ultraviolet irradiation unit of Embodiment 9, and part (B) is a diagram showing a cross section of the ultraviolet irradiation unit of part (A) taken along line A-A.

An ultraviolet irradiation unit 1 of Embodiment 9 will be described with reference to FIG. 19. The ultraviolet irradiation unit 1 of Embodiment 9 is different from the ultraviolet irradiation unit 1 of Embodiment 8 with respect to a feature of including a plurality of heat radiating protruding portions 117 having a rectangular column shape, which protrude from a fluid contact portion 25 of an ultraviolet emission opening side casing 119 toward the direction of ultraviolet irradiation in a long length and which are provided in a half circumferential region of the fluid contact portion 25 in the circumferential direction and spaced apart at intervals.

Figure 20:
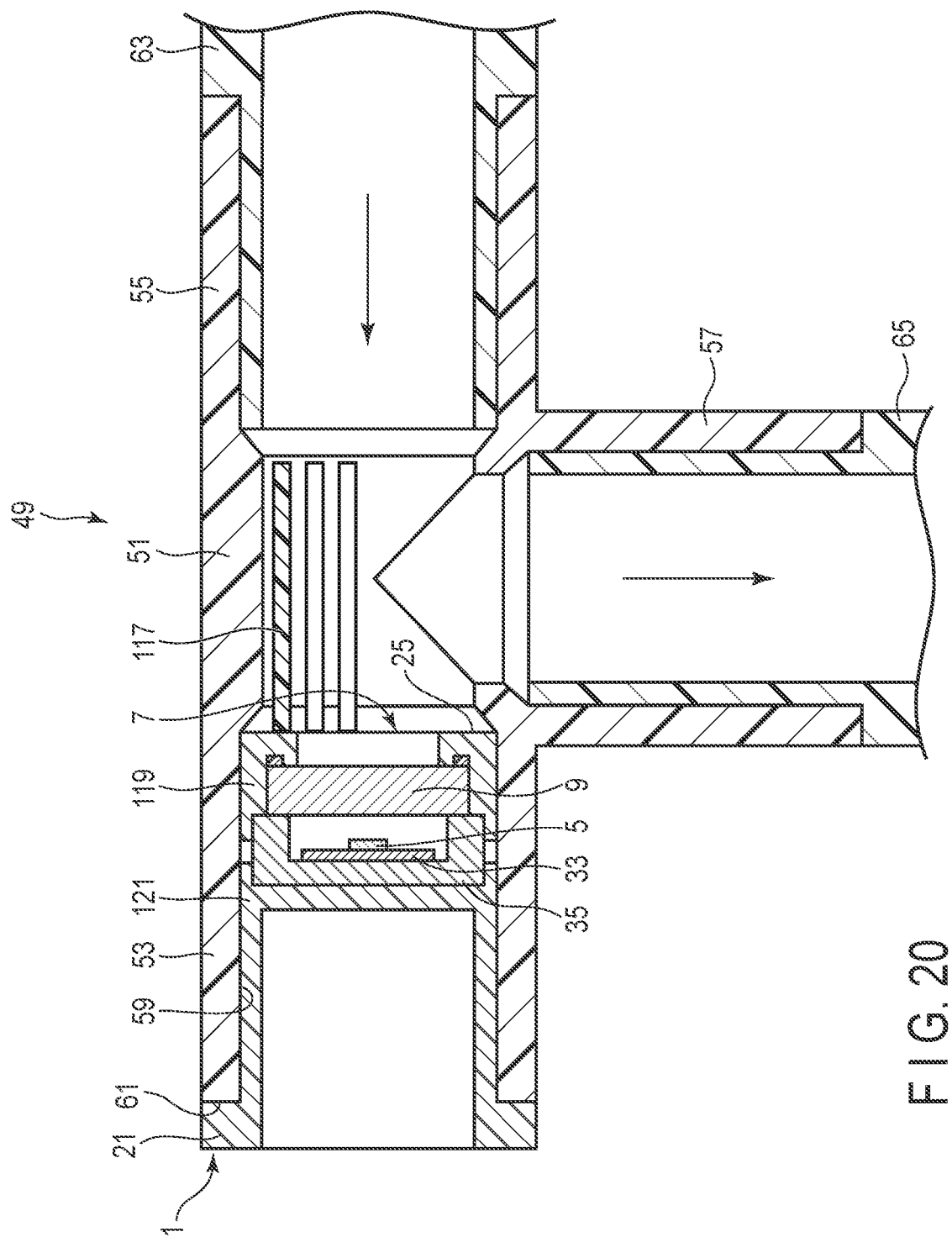
FIG. 20 is a cross-sectional view showing an ultraviolet sterilization device comprising an ultraviolet irradiation unit of Embodiment 9.

As shown in FIG. 20, in the ultraviolet irradiation unit 1 of Embodiment 9, since the casing is divided into the ultraviolet emission opening side casing 119 and the anti-ultraviolet emission opening side casing 121 and includes a plurality of heat radiating protruding portions 117 having a rectangular column shape, heat generated from the light source 5 is moved to the ultraviolet emission opening side casing 119 and the anti-ultraviolet emission opening side casing 121, via a substrate 33 and a base 35, and the heat moved to the ultraviolet emission opening side casing 119 which is the heat radiating portion is moved from a fluid contact portion 25 and the plurality of heat radiating protruding portions 117 having a columnar shape into the fluid. For this reason, the ultraviolet irradiation unit 1 of Embodiment 9 can suppress or prevent the light source 5 becoming in a high temperature state and the premature deterioration of the light source 5 by moving the heat of the light source 5 into the fluid. Furthermore, since the ultraviolet irradiation unit 1 of Embodiment 9 does not include a heat radiating body 39, the costs for the heat radiating body 39 can be reduced.

Embodiment 10

The irradiation intensity of the ultraviolet rays emitted from the ultraviolet irradiation unit 1 is indicated by W/mm$^2$ as described above. The sterilization dose of ultraviolet rays on the fluid is indicated by W·sec/mm$^2$. That is, when the output of the used ultraviolet rays is the same, a higher sterilization rate can be obtained as the irradiation time is longer for the fluid. Therefore, reducing the flow velocity of the fluid in order to increase the irradiation time of the ultraviolet rays to the fluid and improve the sterilization effect.

An ultraviolet sterilization device 49 of Embodiment 10 will be described with reference to FIG. 21. In the ultraviolet sterilization device 49 of Embodiment 10, the ultraviolet irradiation unit 1 is fitted in the first mouth portion 53 which is one mouth portion of the joint 51 including three mouth portions. The ultraviolet irradiation unit 1 is provided at the first mouth portion 53, which is a mouth portion facing the direction of flowing fluid, and an ultraviolet emission opening side casing end portion 127 of the casing 3 is present on the side of a second mouth portion 55 which is the mouth portion facing a first mouth portion 53, i.e., a mouth portion into which the ultraviolet irradiation unit 1 is fitted, beyond an opening 129 of a third mouth portion 57 of the joint 51. In other words, in the ultraviolet irradiation unit 1, a part of the casing 3 is fitted in the first mouth portion 53 so as to face the opening 129 of the third mouth portion 57 of the joint 51 and to be spaced apart therefrom.

Figure 21:
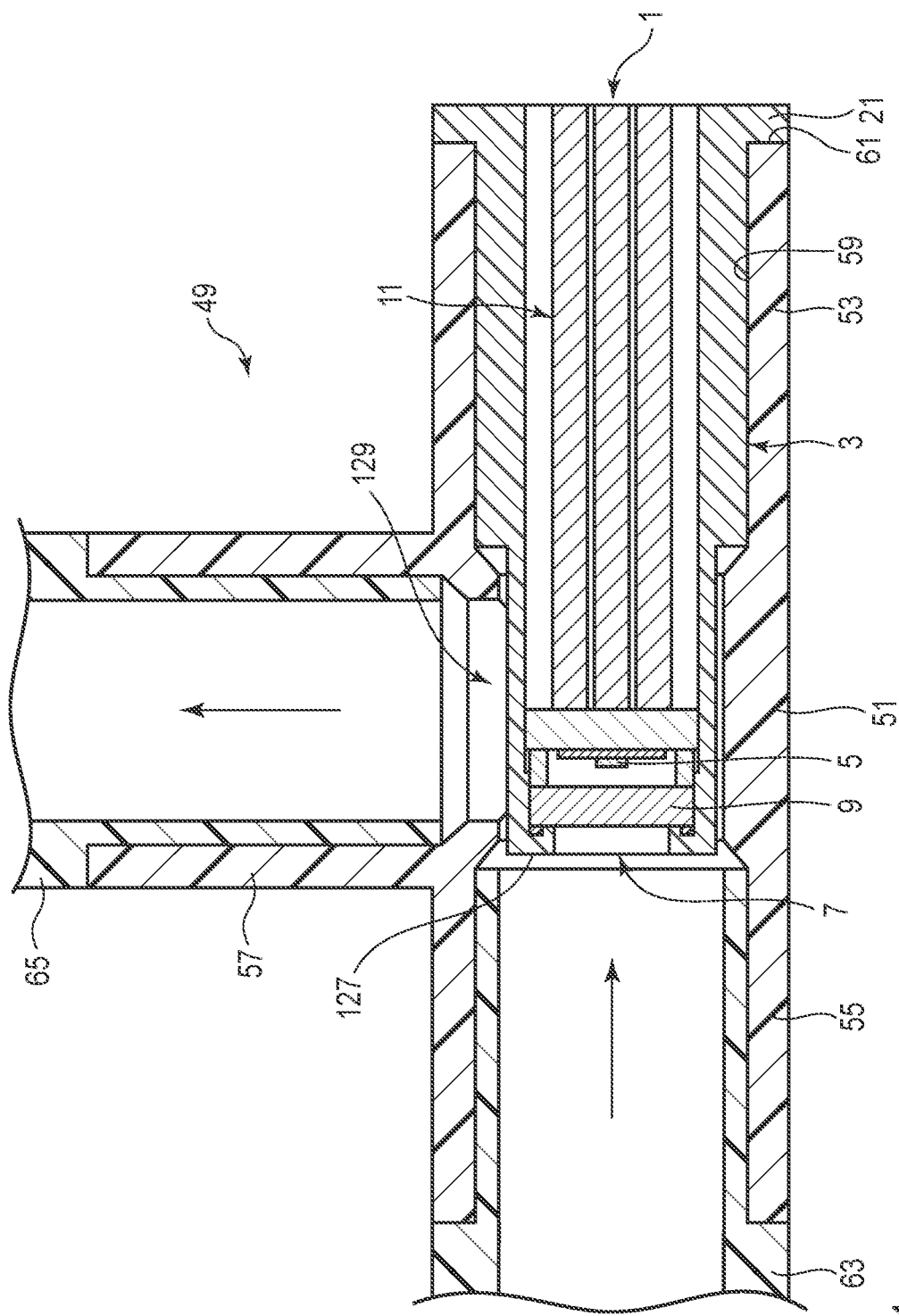
FIG. 21 is cross-sectional view showing an ultraviolet sterilization device of Embodiment 10.

As shown in FIG. 21, in the ultraviolet sterilization device 49 of Embodiment 10, since the ultraviolet emission opening side casing end portion 127 of the casing 3 of the ultraviolet irradiation unit 1 is present on the second mouth portion 55 side beyond the opening 129 of the third mouth portion 57, i.e., since a part of the casing 3 of the ultraviolet irradiation unit 1 is fitted in the first mouth portion 53 so as to face the opening 129 of the third mouth portion 57 of the joint 51 and to be spaced apart therefrom, the flow velocity from the inflow side flow channel pipe 63 to the ultraviolet emission opening side casing end portion 127, of the fluid flowing from inflow side flow channel pipe 63 to the outflow side flow channel pipe 65, can be reduced as compared with the flow velocity in the outflow side flow channel pipe 65. For this reason, in the ultraviolet sterilization device 49 of Embodiment 10, as compared with the ultraviolet sterilization device wherein the casing 3 of the ultraviolet irradiation unit 1 is fitted into the first mouth 53 without facing the opening 129 of the third mouth 57 or being spaced apart therefrom, the irradiation time of the ultraviolet rays applied from the ultraviolet irradiation unit 1 to the fluid flowing from the inflow side flow channel pipe 63 to the ultraviolet emission opening side casing end portion 127 can be extended and the sterilization rate of the fluid can be improved.

Figure 22:
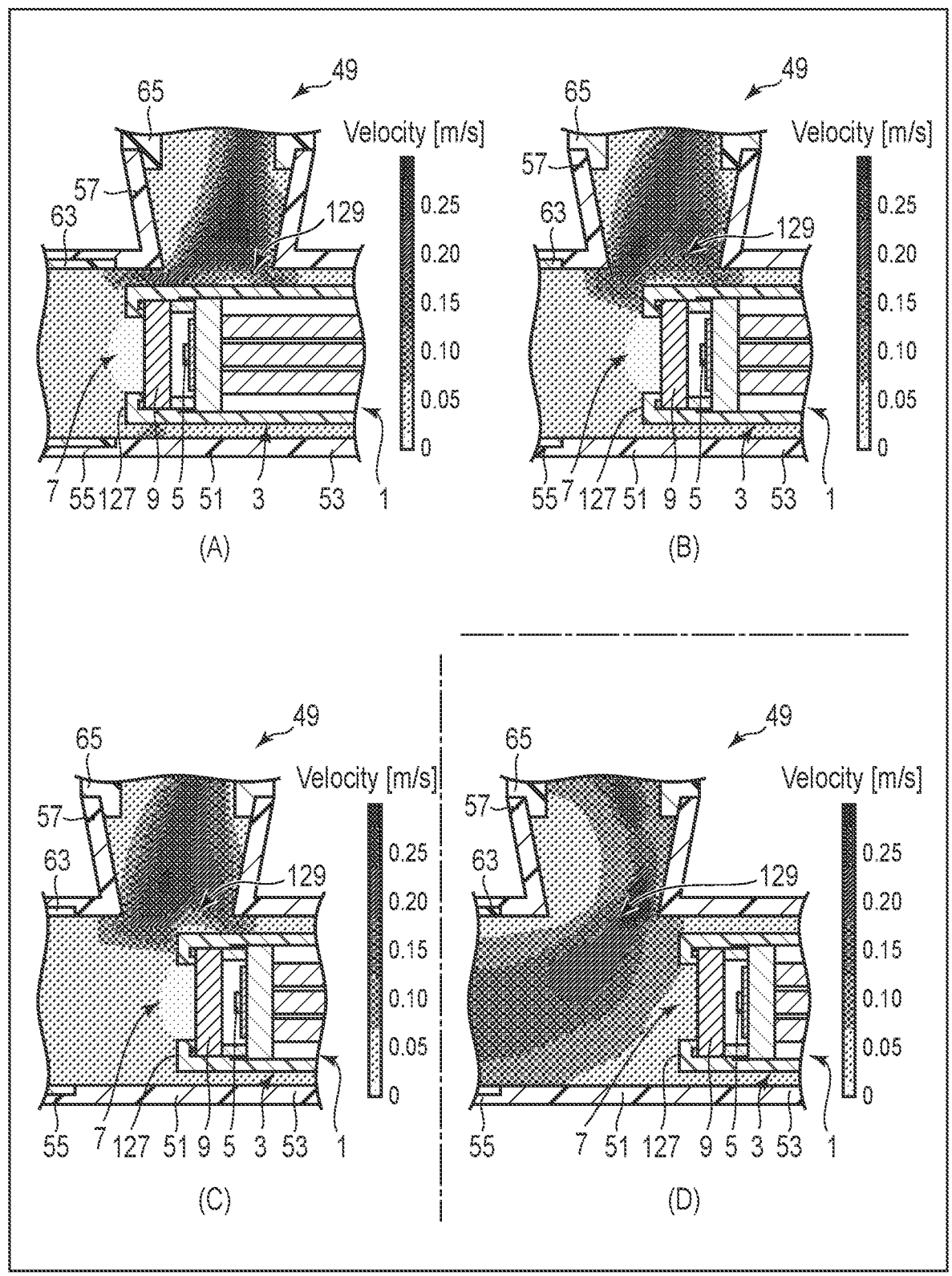
FIG. 22 is a diagram showing comparison of ultraviolet emission opening side casing end parts of a casing of the ultraviolet irradiation unit while positions thereof are changed, where part (A) is a distribution diagram of a velocity of the fluid in the ultraviolet sterilization device of Example 1, part (B) is a distribution diagram of a velocity of the fluid in the ultraviolet sterilization device of Example 2, part (C) is a distribution diagram of a velocity of the fluid in the ultraviolet sterilization device of Example 3, and part (D) is a distribution diagram of a velocity of the fluid in the ultraviolet sterilization device of Example 4.

In order to confirm the flow velocity from the inflow side flow channel pipe 63 to the ultraviolet emission opening side casing end portion 127 and the flow velocity in the outflow side flow channel pipe 65, of the fluid flowing from the inflow side flow channel pipe 63 to the outflow side flow channel pipe 65, in the ultraviolet sterilization device 49 of Embodiment 10, each of the flow velocities of the fluids in the ultraviolet sterilization devices having the configurations of Examples 1 to 4 shown in (A) to (D) of FIG. 22 was measured. The configurations of the ultraviolet sterilization devices of Examples 1 to 4 are described below. The ultraviolet sterilization devices of Examples 1 to 3 correspond to the ultraviolet sterilization device of Embodiment 10.

Example 1 ultraviolet sterilization device 49 in which the ultraviolet emission opening side casing end portion 127 of the casing 3 of the ultraviolet irradiation unit 1 is present on the second mouth portion 55 side beyond the opening 129 of the third mouth portion 57 ((A) of FIG. 22)

Example 2 ultraviolet sterilization device 49 in which the ultraviolet emission opening side casing end portion 127 of the casing 3 of the ultraviolet irradiation unit 1 is present on the second mouth portion 55 side, but is not beyond the opening 129 of the third mouth portion 57 ((B) of FIG. 22)

Example 3 ultraviolet sterilization device 49 in which the ultraviolet emission opening side casing end portion 127 of the casing 3 of the ultraviolet irradiation unit 1 is present on a center line of the opening 129 of the third mouth portion 57 ((C) of FIG. 22)

Example 4 ultraviolet sterilization device 49 in which the casing 3 of the ultraviolet irradiation unit 1 is fitted into the first opening 53 without facing the opening 129 of the third mouth portion 57 and being spaced apart therefrom ((D) of FIG. 22)

The flow velocities of the fluids in the ultraviolet sterilization devices 49 having the configurations of Examples 1 to 4 shown in (A) to (D) of FIG. 22 were measured by a simulation using COMSOL. The simulation in each example was performed under the conditions that the inner diameter of the inflow side flow channel pipe 63 was 31 mm, the inner diameter of the outflow side flow channel pipe 65 and the minimum diameter of the opening of the third mouth portion were 20 mm, and the fluid was supplied to the inflow side flow channel pipe 63 at the flow rate of 2 L and the flow rate of 0.04 m/s.

The flow rates of the fluids of the ultraviolet sterilization device 49 of Embodiment 10 will be described with reference to (A) to (D) of FIG. 22.

As shown in (A) of FIG. 22, it can be understood that, in the ultraviolet sterilization device 49 of Example 1, the velocity of the fluid from the inflow side flow channel pipe 63 to the ultraviolet emission opening side casing end portion 127 is approximately 0.05 m/s from the center of the flow channel pipe over the pipe wall side and the velocity of the fluid in the vicinity of the center of the outflow side flow channel pipe 65 is approximately 0.30 m/s at the maximum.

As shown in (B) of FIG. 22, it can be understood that, in the ultraviolet sterilization device 49 of Example 2, the velocity of the fluid from the inflow side flow channel pipe 63 to the ultraviolet emission opening side casing end portion 127 is approximately 0.05 m/s from the center of the flow channel pipe over the pipe wall side and the velocity of the fluid in the vicinity of the center of the outflow side flow channel pipe 65 is approximately 0.25 m/s at the maximum.

As shown in (C) of FIG. 22, it can be understood that, in the ultraviolet sterilization device 49 of Example 3, the velocity of the fluid from the inflow side flow channel pipe 63 to the ultraviolet emission opening side casing end portion 127 is approximately 0.05 m/s from the center of the flow channel pipe over the pipe wall side and the velocity of the fluid in the vicinity of the center of the outflow side flow channel pipe 65 is approximately 0.25 m/s at the maximum.

As shown in (D) of FIG. 22, it can be understood that, in the ultraviolet sterilization device 49 of Example 4, the velocity of the fluid from the inflow side flow channel pipe 63 to the ultraviolet emission opening side casing end portion 127 is approximately 0.15 m/s in the vicinity of the center of the flow channel pipe and approximately 0.10 m/s on the pipe wall side, and the velocity of the fluid in the vicinity of the center of the outflow side flow channel pipe 65 is approximately 0.25 m/s at the maximum.

For this reason, in the ultraviolet sterilization devices of Examples 1 to 3, which are Embodiment 10, as compared with the ultraviolet sterilization device of Example 4 wherein the casing 3 of the ultraviolet irradiation unit 1 is fitted into the first mouth 53 without facing the opening 129 of the third mouth 57 or being spaced apart therefrom, the irradiation time of the ultraviolet rays applied from the ultraviolet irradiation unit 1 to the fluid flowing from the inflow side flow channel pipe 63 to the ultraviolet emission opening side casing end portion 127 can be extended and the sterilization rate of the fluid can be improved.

Embodiment 11

Figure 23:
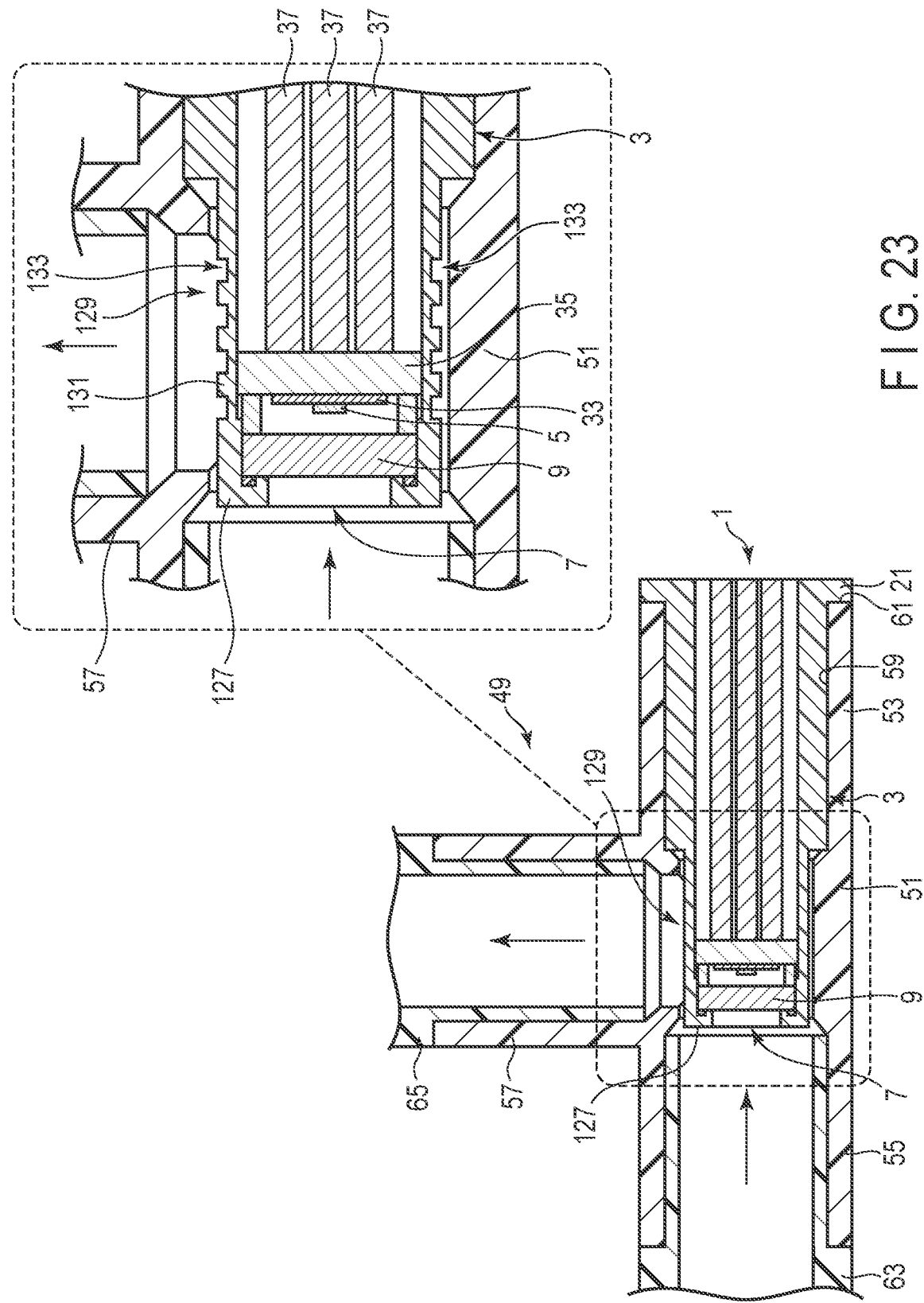
FIG. 23 is cross-sectional view showing an ultraviolet sterilization device according to Embodiment 11.

An ultraviolet sterilization device 49 of Embodiment 11 will be described with reference to FIG. 23. The ultraviolet sterilization device 49 of Embodiment 11 is different from the ultraviolet sterilization device 49 of Embodiment 10 with respect to features that a heat radiating portion 131 is provided at a position facing an opening 129 of a third mouth portion 57 of a joint 51, in the casing 3 so as to be spaced apart therefrom, and that the heat radiating portion 131 is formed of a material having a high thermal conductivity.

The heat radiating portion 131 is provided by forming a plurality of slits 133 at positions facing the opening 129 of the third mouth portion 57 of the joint 51 and being spaced apart therefrom, in the casing 3. The heat radiating portion 131 is formed of the above-mentioned material having a high thermal conductivity. The plurality of slits 133 increase the area in which the casing 3 is in contact with the fluid.

In the ultraviolet sterilization device 49 of Embodiment 11, since the casing 3 includes the heat radiating portion 131 at the position facing the opening 129 of the third opening 57 of the joint 51 and being spaced apart therefrom, the heat generated from the light source 5 is moved to each of heat radiating plates 37 and the casing 3 via the substrate 33 and the base 35. The heat moving to each of the heat radiating plates 37 is released into the atmosphere, and the heat moving to the casing 3 moves from the heat radiating portion 131 into the fluid. For this reason, since the ultraviolet sterilization device 49 of Embodiment 11 improves heat radiation by releasing the heat of the light source 5 into the atmosphere or moving the heat into the fluid, the device can suppress or prevent the light source 5 in a high temperature state at the time of applying the ultraviolet rays, and early deterioration of the light source 5.

Embodiment 12

An ultraviolet sterilization device 49 of Embodiment 12 will be described with reference to FIG. 24. In FIG. 24, the ultraviolet sterilization device 49 of Embodiment 12 is different from the ultraviolet sterilization device 49 of Embodiment 10 with respect to a feature that an inflow side flow channel pipe 63 provided in a second mouth portion 55 of a joint 51 is connected to an upstream side flow channel pipe 137 via a 90-degree elbow type joint 135.

In FIG. 24, the ultraviolet sterilization device 49 of Embodiment 12 is located at a position lower than the upstream side flow channel pipe 137 in the flow channel when the direction parallel to the inflow side flow channel pipe 63 is the first direction X, the direction parallel to the outflow side flow channel pipe 65 and the upstream side flow channel pipe 137 is the second direction Y, the first direction X and the second direction Y are orthogonal to each other, and the positive direction of the second direction Y is defined as upward or upside.

As shown in FIG. 24, since the ultraviolet sterilization device 49 of Embodiment 12 is arranged at a low position in the flow channel, air bubbles such as air entering the second mouth portion 55 and the inflow side flow channel pipe 63 can be suppressed or prevented. For this reason, in the ultraviolet sterilization device 49 of Embodiment 12, directly applying the ultraviolet rays applied from the ultraviolet irradiation unit 1, to the second mouth portion 55 and the inner diameter surface of the second mouth portion 55 and the premature deterioration of the second mouth portion 55 and the inflow side flow channel pipe 63 can be suppressed or prevented. In addition, a decrease in the sterilization rate caused by bubbles can be suppressed or prevented.

Embodiment 13

Figure 25:
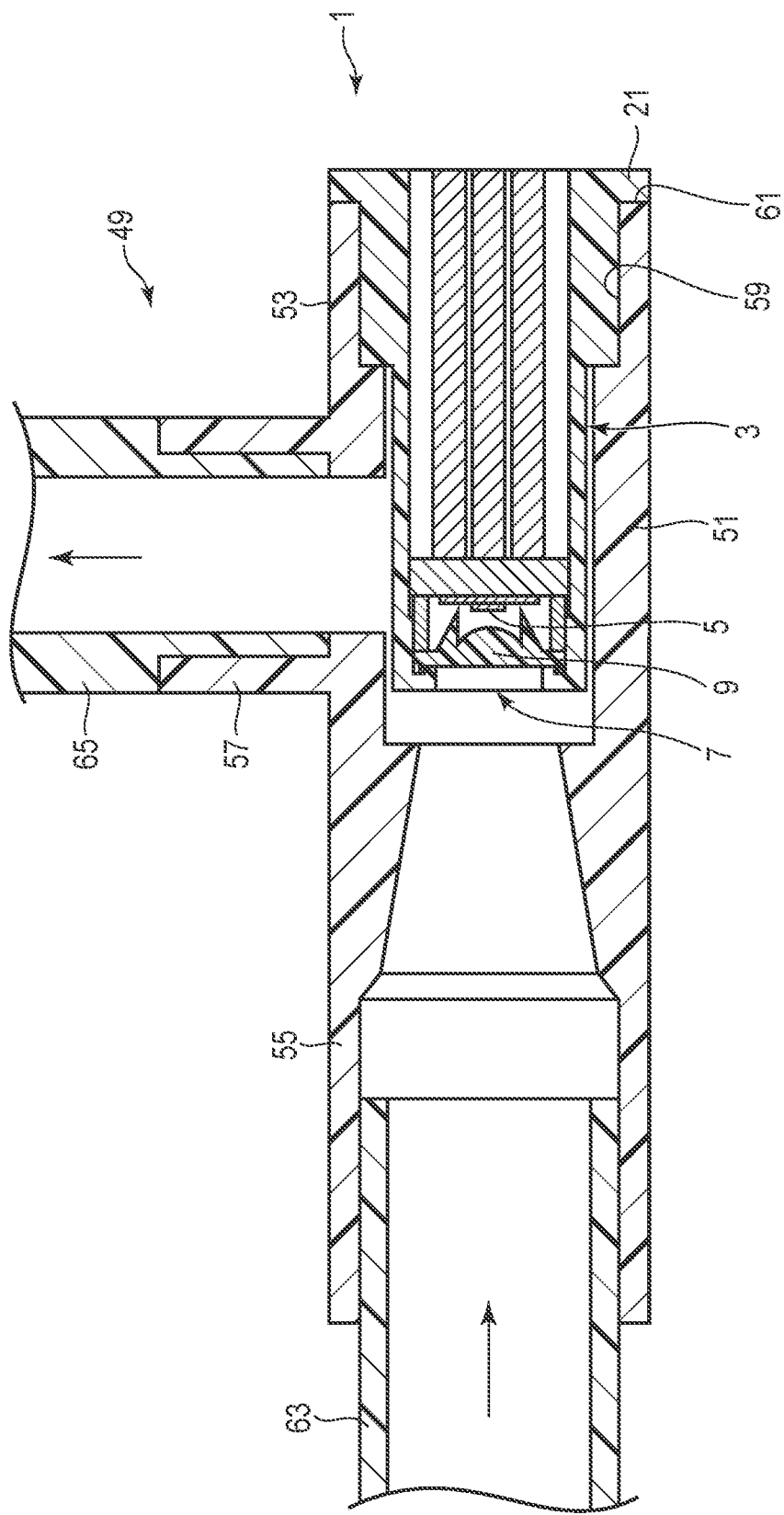
FIG. 25 is cross-sectional view showing an ultraviolet sterilization device according to Embodiment 13.

An ultraviolet sterilization device 49 of Embodiment 13 will be described with reference to FIG. 25 and FIG. 26. In FIG. 25, the ultraviolet sterilization device 49 of Embodiment 13 is different from the ultraviolet sterilization device 49 of Embodiment 10 with respect to features that the ultraviolet irradiation unit 1 of Embodiment 4 including the ultraviolet transmitting body 9 which is a condenser lens is fitted in a first mouth portion 53 of a joint 51 and that an inner diameter dimension of a second mouth portion 55 of the joint 51 becomes smaller toward the first mouth portion 53.

As shown in FIG. 26, the inner diameter dimension of the second mouth portion 55 of the joint 51 of Embodiment 13 is gradually smaller from $\phi 1$ toward $\phi 2$ toward the first mouth portion 53. In FIG. 25, $\phi 1$ is the same as the inner diameter dimension of an inflow side flow channel pipe 63 that is inserted and connected to the second mouth portion 55. $\phi 2$ is larger than or equal to the inner diameter dimension of an ultraviolet emission opening 7 of the casing 3 of the ultraviolet irradiation unit 1 and is, for example, 90% to 50% of the inner diameter dimension of $\phi 1$.

As shown in FIG. 25, in the ultraviolet sterilization device 49 of Embodiment 13, since the inner diameter dimension of the second mouth portion 55 of the joint 51 is smaller toward the first mouth portion 53, the fluid flowing from the inflow side flow channel pipe 63 to the outflow side flow channel pipe 65 can be collected near the center of the pipe in a second mouth portion 55. Then, the ultraviolet sterilization device 49 of Embodiment 13 can improve the sterilization rate of the fluid by irradiating the fluid collected near the center of the pipe in the second mouth portion 55 with ultraviolet rays having a high ultraviolet intensity.

Figure 27:
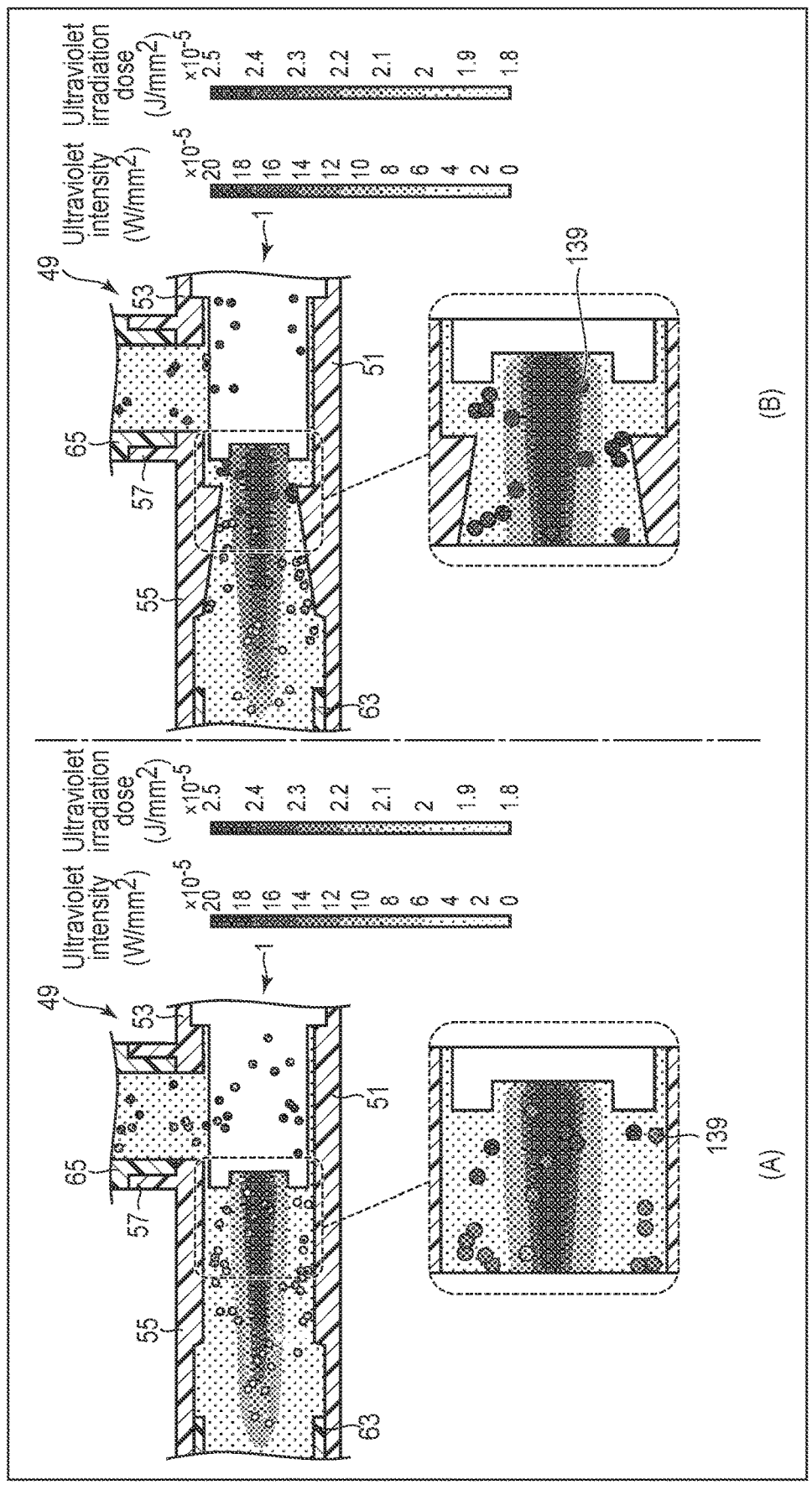
FIG. 27 is a diagram showing comparison of ultraviolet sterilization devices while joints thereof are changed, where part (A) is a diagram showing an irradiation dose of ultraviolet rays to which particles flowing in the ultraviolet sterilization device of Example 5 are exposed, and an intensity distribution of ultraviolet rays irradiated from the ultraviolet irradiation unit, and part (B) is a diagram showing an irradiation dose of ultraviolet rays to which particles flowing in the ultraviolet sterilization device of Example 6 are exposed, and an intensity distribution of ultraviolet rays irradiated from the ultraviolet irradiation unit.

In order to confirm the improvement of the sterilization rate of the fluid in the ultraviolet sterilization device 49 of Embodiment 13, simulation using COMSOL was performed with the ultraviolet sterilization devices of the configurations of Examples 5 and 6 shown in (A) and (B) of FIG. 27. Each of the structures of the ultraviolet sterilization devices of Examples 5 and 6 and the conditions of the simulation are mentioned below. Incidentally, in (A) and (B) of FIG. 27, the ultraviolet irradiation unit 1 is shown on a colored background.

Example 5 ultraviolet sterilization device 49 in which the inner diameter dimension of the second mouth portion 55 of the joint 51 is constant at 25 mm toward the first mouth portion 53 (for example, $\phi 1=\phi 2=25$ mm in FIG. 26) ((A) in FIG. 27)

Example 6 ultraviolet sterilization device 49 in which the inner diameter dimension of the second mouth portion 55 of the joint 51 is 25 mm to 18 mm toward the first mouth portion 53 (for example, $\phi 1=25$ mm and $\phi 2=18$ mm in FIG. 26) ((B) in FIG. 27)

Simulation conditions: In the ultraviolet sterilization devices having the configurations of Examples 5 and 6, a fluid containing 1,000 particles simulating the cells was supplied at a flow rate of 2 L/min from the inflow side flow channel pipe 63 toward the outflow side flow channel pipe 65.

By the above simulation, the intensity distribution of the ultraviolet rays emitted from the ultraviolet irradiation unit, in the ultraviolet sterilization devices having the configurations of Examples 5 and 6, and the irradiation dose of the ultraviolet rays to which the particles flowing in the ultraviolet sterilization devices were exposed were measured.

Figure 28:
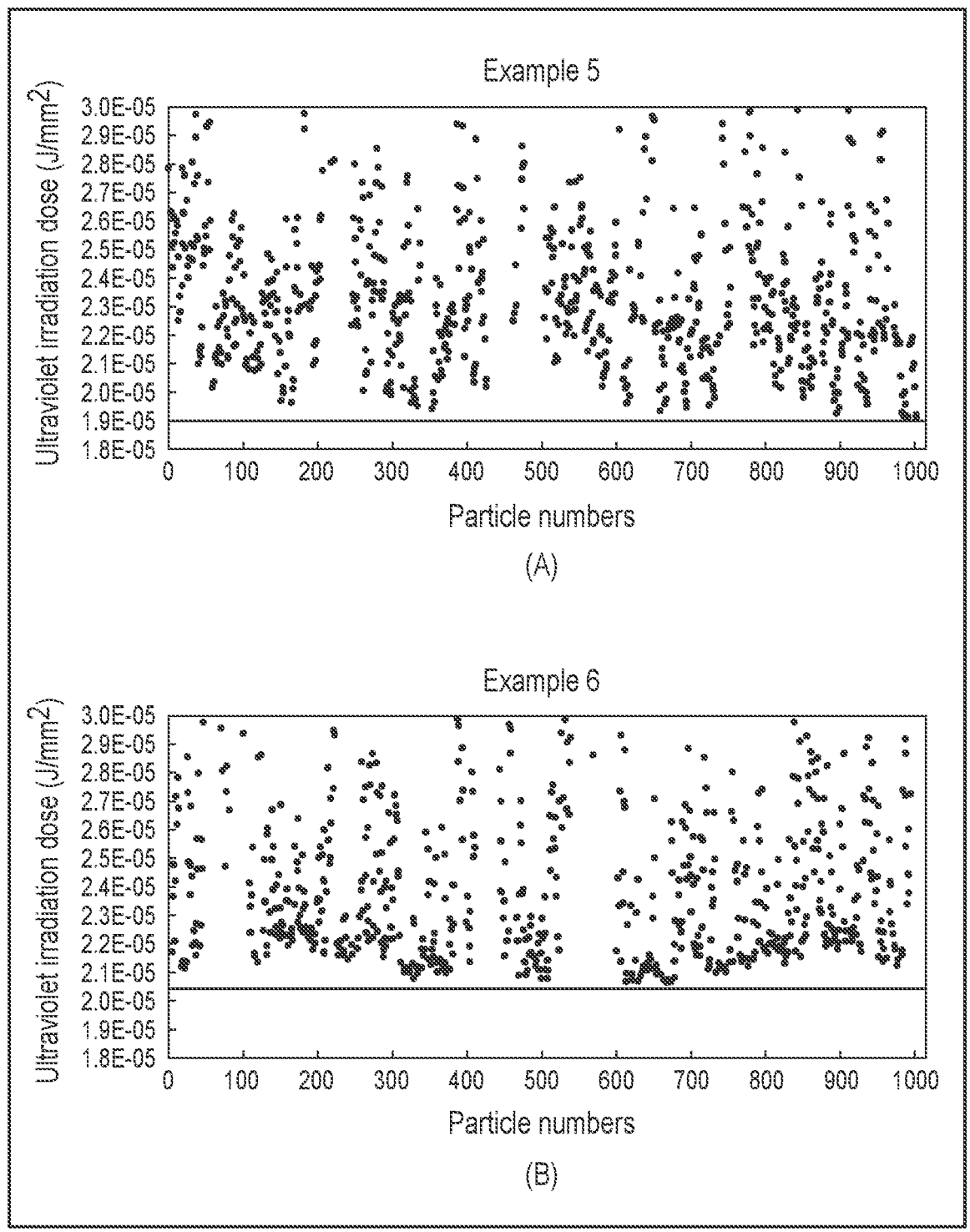
FIG. 28, part (A) is a graph showing the irradiation dose of ultraviolet rays to which particles are exposed, in the ultraviolet sterilization device of Example 5, and part (B) is a graph showing the irradiation dose of ultraviolet rays to which particles are exposed, in the ultraviolet sterilization device of Example 6.

The irradiation dose of the ultraviolet rays to which the particles were exposed corresponds to the sterilization rate of the fluid by the ultraviolet sterilization devices, and the irradiation dose of the ultraviolet rays to which each particle was exposed is shown in FIG. 28. In graphs of (A) and (B) of FIG. 28, the horizontal axis represents the serial numbers assigned to 1,000 particles, and the vertical axis represents the irradiation dose of the ultraviolet rays to which each particle was exposed. Incidentally, in FIG. 28, the plot of particles of the ultraviolet irradiation dose exceeding 3.0× E−5 J/mm² is omitted.

The irradiation dose of the ultraviolet rays to which 1,000 particles flowing in the ultraviolet sterilization device 49 of the configurations of Examples 5 and 6 were exposed will be described with reference to (A) and (B) of FIG. 27 and (A) and (B) of FIG. 28.

It can be understood that in the ultraviolet sterilization device 49 of Example 5, as shown in (A) of FIG. 27, some of the particles 139 contained in the fluid are flowing on the pipe wall side of the pipe having a lower ultraviolet intensity as compared with that of the vicinity of the center of the pipe in the second mouth portion 55. In addition, it can be understood that as shown in (A) of FIG. 28, the minimum ultraviolet irradiation dose of 1,000 particles is 1.9×E−5 J/mm².

In contrast, it can be understood that in the ultraviolet sterilization device 49 of Example 6, as shown in (B) of FIG. 27, the particles 139 contained in the fluid are flowing near the center of the pipe having a higher ultraviolet intensity as compared with that on the pipe wall side of the pipe, in the second port 55. In addition, it can be understood that as shown in (B) of FIG. 28, the minimum ultraviolet irradiation dose of 1,000 particles is 2.07×E−5 J/mm². It can be understood that in the ultraviolet sterilization device 49 of Example 6, the minimum ultraviolet irradiation dose of 1,000 particles is improved by approximately 9% as compared with the ultraviolet sterilization device 49 of Example 5.

Therefore, in the ultraviolet sterilization device of Example 6, which is Embodiment 13, since the inner diameter dimension of the second mouth portion 55 of the joint 51 becomes smaller toward the first mouth portion 53, the sterilization rate of the fluid can be improved by collecting the fluid flowing from the inflow side flow channel pipe 63 to the outflow side flow channel pipe 65, in the vicinity of the center of the pipe in the second mouth portion 55, and irradiating the fluid with ultraviolet rays having a high ultraviolet intensity.

Modified Example

The present invention is not limited to the embodiments described above, and the constituent elements of the invention can be modified in various ways without departing from the spirit and scope of the invention.

Figure 29:
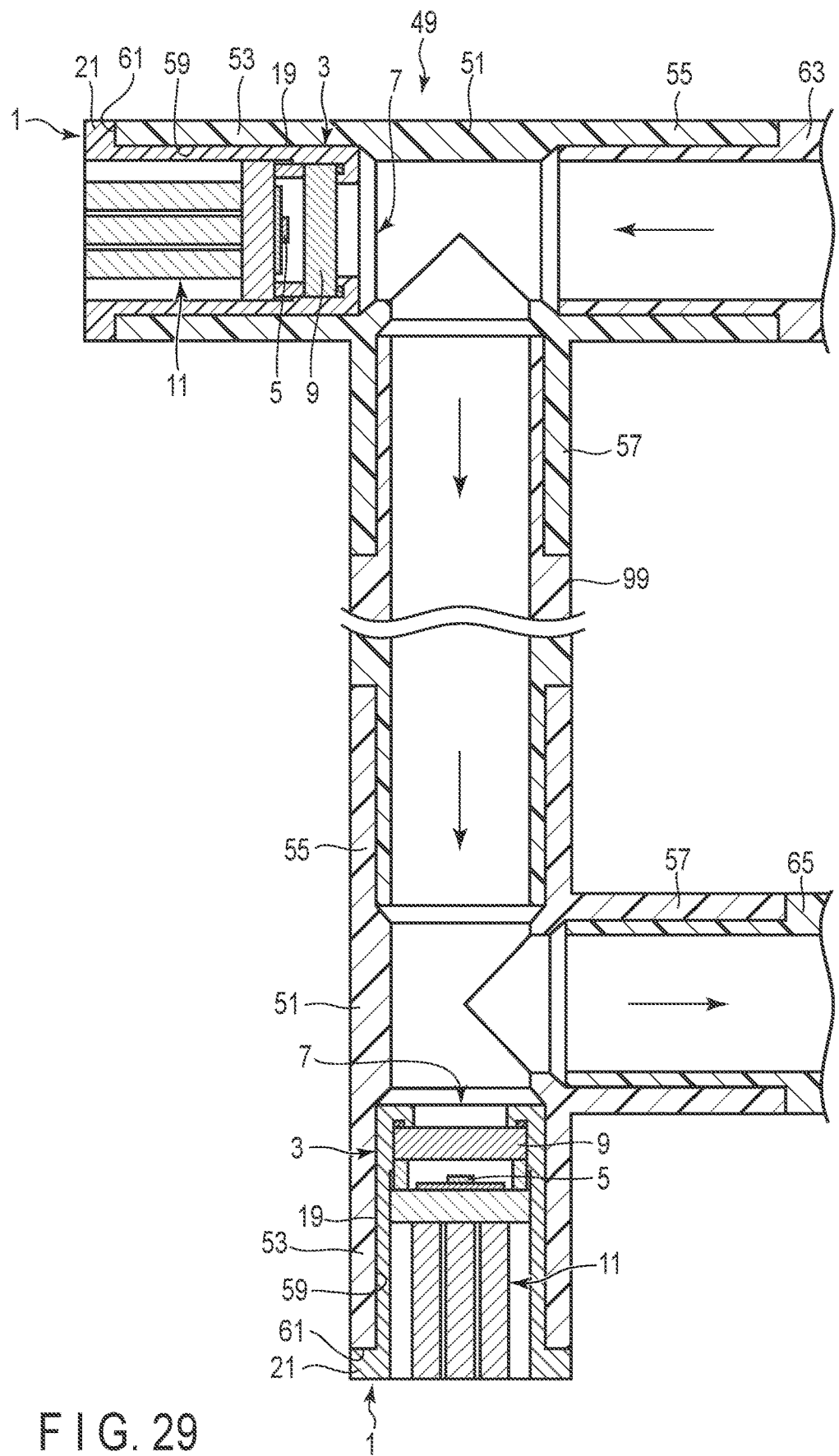
FIG. 29 is a cross-sectional view showing an ultraviolet sterilization device of Modified Example 1.

As shown in FIG. 29, the ultraviolet sterilization device 49 may include two joints 51 connected via a flow channel pipe 99 and the ultraviolet irradiation unit 1 fitted in the first mouth portion 53 of each joint 51. The flow channel pipe 99 is an existing channel pipe and is fixed to mouth portions of two joints 51 by, for example, screws, an adhesive, welding, or the like.

Since the ultraviolet sterilization device 49 shown in FIG. 29 comprises two ultraviolet irradiation units 1, the time to irradiate the fluid with ultraviolet rays can be made longer and the amount of the fluid to be sterilized can be increased.

The ultraviolet sterilization device 49 includes, for example, one to ten sets of the ultraviolet irradiation units 1 and the joints 51 where one ultraviolet irradiation unit 1 and one joint 51 are handled as one set.

Figure 30:
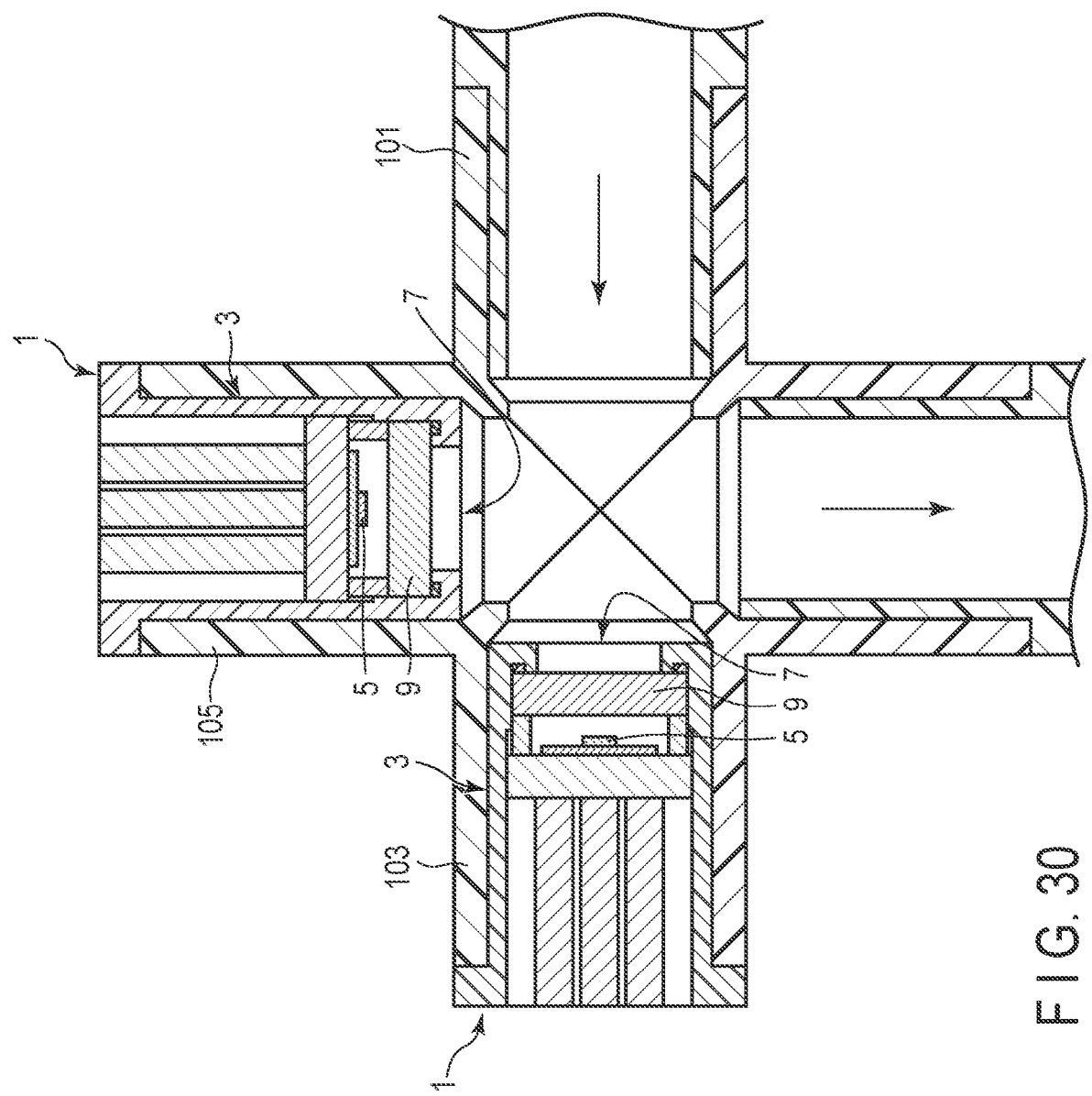
FIG. 30 is a cross-sectional view showing an ultraviolet sterilization device of Modified Example 2.

As shown in FIG. 30, the ultraviolet sterilization device 49 may include a joint 101 including four mouth portions, and two ultraviolet irradiation units 1 fitted in a first mouth portion 103 and a second mouth portion 105 which are two mouth portions of the joint 101. Incidentally, the ultraviolet sterilization device 49 shown in FIG. 30 may comprise the ultraviolet irradiation unit 1 fitted in the first mouth portion 103 and, instead of the ultraviolet irradiation unit 1, a plug (not shown) may be fitted in the second mouth portion 105.

For example, the plurality of heat radiating protruding portions 117 may have a hemispherical shape instead of a rectangular parallelepiped shape, and the heat radiating protruding portions having a rectangular parallelepiped shape and the heat radiating protruding portions having a hemispherical shape may be provided alternately. In addition, for example, the plurality of heat radiating protruding portions 117 may have a columnar shape instead of a rectangular column shape, and the heat radiating protruding portions having a columnar shape and the heat radiating protruding portions having a rectangular column shape may be provided alternately.

In the casing 3 of the ultraviolet sterilization device 49 of Embodiment 10, the outer diameter of the portion facing the opening 129 of the third mouth portion 57 of the joint 51 so as to be spaced apart therefrom may have the same outer diameter as the outer diameter of the portion which abuts one the first mouth portion 53 of the joint 51.

In the ultraviolet sterilization device 49 of Embodiment 12, the upstream side flow channel pipe 137 connected to the inflow side flow channel pipe 63 provided at the second mouth portion 55 of the joint 51 may be arranged above the ultraviolet sterilization device 49, and may be arranged above the other upstream side flow channel pipes and downstream side flow channel pipes.

The inner diameter dimension of the second mouth portion 55 of the joint 51 of Embodiment 13 may be made gradually smaller toward the first mouth portion 53.

In Embodiment 13, the ultraviolet irradiation unit 1 may be the ultraviolet irradiation unit 1 of Embodiment 3 instead of the ultraviolet irradiation unit 1 of Embodiment 4.

In the joint 51 of the ultraviolet sterilization device 49 of Embodiment 13, as shown in FIG. 31, the first mouth portion 53 of the joint 51 and the casing 3 of the ultraviolet irradiation unit 1 may be formed integrally.

Figure 32:
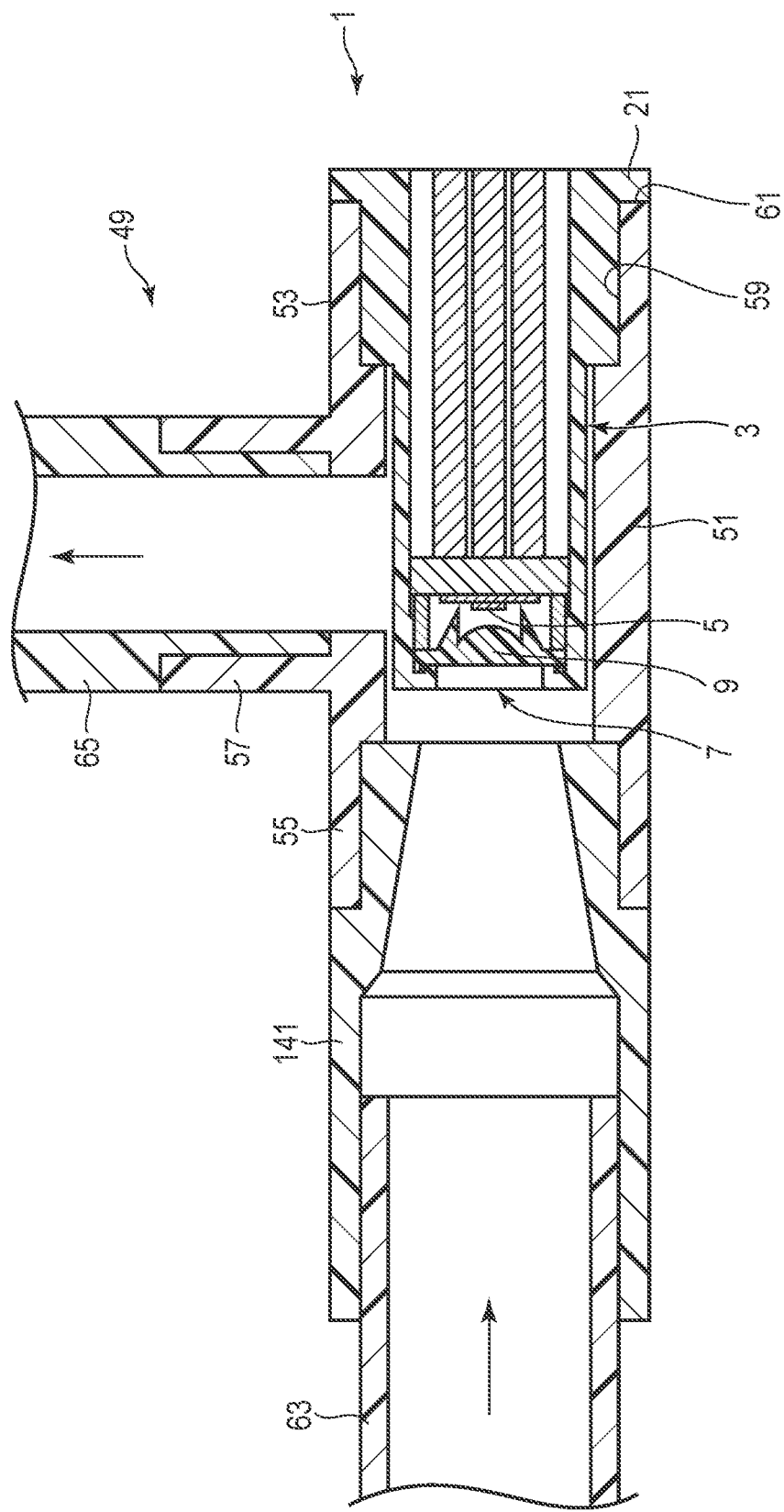
FIG. 32 is a cross-sectional view showing an ultraviolet sterilization device of Modified Example 4.

In the ultraviolet sterilization device 49 of Embodiment 13, as shown in FIG. 32, the inner diameter dimension of the second mouth portion 55 of the joint 51 may be smaller toward the first mouth portion 53 by fitting an inner diameter converting member 141 into the second mouth portion 55.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultraviolet sterilization device comprising
an ultraviolet irradiation unit and a flow channel pipe,
the flow channel pipe includes a joint,
the ultraviolet irradiation unit, comprising:
a casing;
a light source emitting ultraviolet rays arranged in the casing; and
an ultraviolet transmitting body arranged between an ultraviolet emission opening of the casing and the light source, the casing having an outer diameter dimension that enables the casing to fit within a bore of the joint connected to the flow channel pipe,
the flow channel pipe having an inflow side channel pipe and an outflow side channel pipe,
the joint includes a second mouth portion connected to the inflow side channel pipe, a third mouth portion connected to the outflow side channel pipe and a first mouth portion opposed to the second mouth portion,
the ultraviolet irradiation unit being arranged in the first mouth portion where an end part of the casing on the side of the ultraviolet emission opening is in the second mouth portion and extends beyond the opening of the third mouth portion.

2. The ultraviolet sterilization device of claim 1, wherein the ultraviolet sterilization device is arranged at a lowest position in the flow channel pipe.

3. The ultraviolet sterilization device of claim 1, wherein the ultraviolet irradiation unit including the ultraviolet transmitting body which is a condenser lens is fitted in the first mouth portion of the joint, and an inner diameter dimension of the second mouth portion of the joint becomes smaller toward the first mouth portion.

\* \* \* \* \*